United States Patent
Hill et al.

(10) Patent No.: US 9,181,487 B2
(45) Date of Patent: Nov. 10, 2015

(54) PROCESS FOR PREPARING ETHYLENEDIALKYLPHOSPHINIC ACIDS, ESTERS AND SALTS BY MEANS OF ACETYLENE AND USE THEREOF

(75) Inventors: Michael Hill, Cologne (DE); Werner Krause, Huerth (DE); Martin Sicken, Cologne (DE)

(73) Assignee: Clariant Finance (BVI) Limited, Tortola (VG)

(*) Notice: Subject to any disclaimer, the term of this patent is extended or adjusted under 35 U.S.C. 154(b) by 0 days.

(21) Appl. No.: 13/140,212

(22) PCT Filed: Dec. 15, 2009

(86) PCT No.: PCT/EP2009/008964
§ 371 (c)(1),
(2), (4) Date: Jun. 16, 2011

(87) PCT Pub. No.: WO2010/069545
PCT Pub. Date: Jun. 24, 2010

(65) Prior Publication Data
US 2011/0251312 A1 Oct. 13, 2011

(30) Foreign Application Priority Data
Dec. 18, 2008 (DE) .......................... 10 2008 063 626

(51) Int. Cl.
*C07F 9/32* (2006.01)
*C07F 9/30* (2006.01)
*C08K 5/5313* (2006.01)
*C09K 21/12* (2006.01)

(52) U.S. Cl.
CPC ................ *C09K 21/12* (2013.01); *C07F 9/305* (2013.01); *C07F 9/3235* (2013.01); *C08K 5/5313* (2013.01)

(58) Field of Classification Search
None
See application file for complete search history.

(56) References Cited

U.S. PATENT DOCUMENTS

| | | | |
|---|---|---|---|
| 3,345,432 A | 10/1967 | Gillham et al. | |
| 3,784,638 A | 1/1974 | Lambert | |
| 3,875,263 A | 4/1975 | Herwig et al. | |
| 3,939,050 A | 2/1976 | Kleiner et al. | |
| 3,941,752 A | 3/1976 | Kleiner et al. | |
| 3,962,194 A | 6/1976 | Bollert et al. | |
| 4,001,352 A | 1/1977 | Kleiner et al. | |
| 4,035,343 A | 7/1977 | Bollert et al. | |
| 4,069,245 A | 1/1978 | Dursch et al. | |
| 4,069,247 A | 1/1978 | Kleiner | |
| 4,079,049 A | 3/1978 | Ramsey et al. | |
| 4,168,267 A | 9/1979 | Petrillo | |
| 4,235,991 A | 11/1980 | Digiacomo | |
| 4,337,201 A | 6/1982 | Petrillo | |
| 4,374,131 A | 2/1983 | Petrillo | |
| 4,381,297 A | 4/1983 | Karanewsky et al. | |
| 4,427,665 A | 1/1984 | Karanewsky et al. | |
| 4,555,506 A | 11/1985 | Karanewsky et al. | |
| 4,594,199 A | 6/1986 | Thottathil | |
| 4,602,092 A | 7/1986 | Thottathil et al. | |
| 4,634,689 A | 1/1987 | Witkowski et al. | |
| 5,013,863 A | 5/1991 | Baylis et al. | |
| 5,153,347 A | 10/1992 | Lloyd | |
| 5,190,934 A | 3/1993 | Mickel et al. | |
| 5,229,379 A | 7/1993 | Marescaux et al. | |
| 5,391,743 A | 2/1995 | Ebetino et al. | |
| 5,407,922 A | 4/1995 | Marescaux et al. | |
| 5,545,631 A | 8/1996 | Marescaux | |
| 5,739,123 A | 4/1998 | Norcini et al. | |
| 5,780,534 A | 7/1998 | Kleiner et al. | |
| 6,013,707 A | 1/2000 | Kleiner et al. | |
| 6,090,968 A | 7/2000 | Horold et al. | |
| 6,214,812 B1 | 4/2001 | Karpeisky | |
| 6,278,012 B1 * | 8/2001 | Horold et al. | 558/110 |
| 6,355,832 B1 | 3/2002 | Weferling et al. | |
| 6,384,022 B1 | 5/2002 | Jackson et al. | |
| 6,569,974 B1 | 5/2003 | Sicken et al. | |
| 6,583,315 B2 | 6/2003 | Sicken et al. | |
| 6,727,335 B2 | 4/2004 | Sicken et al. | |
| 6,855,757 B2 | 2/2005 | Horold et al. | |

(Continued)

FOREIGN PATENT DOCUMENTS

AT 243952 12/1965
DE 1494922 6/1969

(Continued)

OTHER PUBLICATIONS

Nifant'ev, E. E.; Solovetskaya, L. A.; Maslennikova, V. I.; Magdeeva, R. K.; Sergeev, N. M. Reaction of acetylenes with hypophosphorous and phosphonous acids. Zhurnal Obshchei Khimii. 1986, 56, 773-781 (only as CASREACT printout of abstract, structure, and reactions).*

(Continued)

*Primary Examiner* — Michael Barker
*Assistant Examiner* — Po-Chih Chen
(74) *Attorney, Agent, or Firm* — Anthony A. Bisulca

(57) ABSTRACT

A process for preparing ethylenedialkylphosphinic acids, ethylenedialkylphosphinic esters and ethylenedialkylphosphinic salts, wherein a) a phosphinic acid source (I) is reacted with olefins (IV) in the presence of a catalyst A to give an alkylphosphonous acid, its salt or ester (II), b) the resultant alkylphosphonous acid, its salt or ester (II) is reacted with an acetylenic compound (V) in the presence of a catalyst B, to give the ethylenedialkylphosphinic acid derivative (III), and the catalyst A comprises transition metals, transition-metal compounds and/or catalyst systems which are composed of a transition metal and/or a transition-metal compound and at least one ligand, and the catalyst B comprises peroxide-forming compounds, peroxo compounds and/or azo compounds.

5 Claims, No Drawings

(56) References Cited

U.S. PATENT DOCUMENTS

| | | |
|---|---|---|
| 7,446,140 B2 | 11/2008 | Bauer |
| 7,473,794 B2 | 1/2009 | Wehner et al. |
| 7,485,745 B2 | 2/2009 | Maas et al. |
| 7,749,985 B2 | 7/2010 | Gallop et al. |
| 7,829,736 B2 | 11/2010 | Wehner et al. |
| 8,084,518 B2 | 12/2011 | Bauer |
| 8,097,753 B2 | 1/2012 | Maas et al. |
| 2002/0187977 A1 | 12/2002 | Pearlman et al. |
| 2003/0073865 A1 | 4/2003 | Sicken et al. |
| 2003/0171466 A1 | 9/2003 | Horold et al. |
| 2003/0216533 A1 | 11/2003 | Sicken et al. |
| 2005/0101708 A1 | 5/2005 | Knop et al. |
| 2005/0187196 A1 | 8/2005 | Madrid et al. |
| 2006/0084734 A1 | 4/2006 | Bauer et al. |
| 2006/0194973 A1 | 8/2006 | Gainer et al. |
| 2006/0264654 A1 | 11/2006 | Wehner |
| 2007/0210288 A1 | 9/2007 | Maas et al. |
| 2007/0213436 A1 | 9/2007 | Maas et al. |
| 2007/0213563 A1 | 9/2007 | Maas et al. |
| 2008/0183009 A1 | 7/2008 | Wehner et al. |
| 2008/0214708 A1 | 9/2008 | Bauer et al. |
| 2009/0286759 A1 | 11/2009 | Gallop et al. |
| 2010/0093239 A1 | 4/2010 | Bauer et al. |
| 2011/0201732 A1 | 8/2011 | Hill et al. |
| 2011/0201733 A1 | 8/2011 | Hill et al. |
| 2011/0213052 A1 | 9/2011 | Hill et al. |
| 2011/0213059 A1 | 9/2011 | Hill et al. |
| 2011/0213060 A1 | 9/2011 | Hill et al. |
| 2011/0213061 A1 | 9/2011 | Hill et al. |
| 2011/0213062 A1 | 9/2011 | Hill et al. |
| 2011/0213078 A1 | 9/2011 | Hill et al. |
| 2011/0213079 A1 | 9/2011 | Hill et al. |
| 2011/0213080 A1 | 9/2011 | Hill et al. |
| 2011/0224339 A1 | 9/2011 | Hill et al. |
| 2011/0224340 A1 | 9/2011 | Hill et al. |
| 2011/0237720 A1 | 9/2011 | Hill et al. |
| 2011/0237721 A1 | 9/2011 | Hill et al. |
| 2011/0237722 A1 | 9/2011 | Hill et al. |
| 2011/0245385 A1 | 10/2011 | Hill et al. |
| 2011/0245386 A1 | 10/2011 | Hill et al. |
| 2011/0251310 A1 | 10/2011 | Hill et al. |
| 2011/0251314 A1 | 10/2011 | Hill et al. |
| 2011/0251315 A1 | 10/2011 | Hill et al. |
| 2011/0275744 A1 | 11/2011 | Hill et al. |
| 2011/0281983 A1 | 11/2011 | Hill et al. |
| 2012/0064790 A1 | 3/2012 | Bauer et al. |

FOREIGN PATENT DOCUMENTS

| | | |
|---|---|---|
| DE | 2236036 | 2/1974 |
| DE | 2236037 | 2/1974 |
| DE | 2302523 | 2/1974 |
| DE | 2302523 | 8/1974 |
| DE | 2441878 | 3/1976 |
| DE | 2623775 | 12/1976 |
| DE | 2942781 | 4/1980 |
| DE | 10153780 | 11/2002 |
| DE | 19912920 | 9/2009 |
| EP | 00858391 | 8/1983 |
| EP | 0319482 | 6/1989 |
| EP | 0463560 | 1/1992 |
| EP | 0699708 | 3/1996 |
| EP | 0906915 | 4/1999 |
| EP | 0969008 | 1/2000 |
| EP | 1203770 | 5/2002 |
| EP | 1217004 | 6/2002 |
| EP | 1369422 | 12/2003 |
| EP | 1403311 | 3/2004 |
| EP | 1607400 | 12/2005 |
| EP | 1693403 | 8/2006 |
| EP | 1832594 | 9/2007 |
| EP | 1832595 | 9/2007 |
| EP | 1832596 | 9/2007 |
| EP | 1905776 | 4/2008 |
| GB | 1045684 | 10/1966 |
| JP | 05230085 | 9/1993 |
| SU | 314758 A1 * | 4/1970 |
| WO | WO 99/28327 | 6/1999 |
| WO | WO 01/42252 | 6/2001 |
| WO | WO 0157050 | 8/2001 |
| WO | WO 02/100871 | 12/2002 |
| WO | WO 2005/014604 | 2/2005 |
| WO | WO 2005/032494 | 4/2005 |
| WO | WO 2005/044830 | 5/2005 |
| WO | WO 2007/052169 | 5/2007 |
| WO | WO 2008/033572 | 3/2008 |
| WO | WO 2008/043499 | 4/2008 |

OTHER PUBLICATIONS

CASREACT printout of "Nifant'ev et al., Reaction of acetylenes with hypophosphorous and phosphonous acids. Zhurnal Obshchei Khimii 1986, 56, 773-781."*
Nifant'ev et al., Reaction of acetylenes with hypophosphorous and phosphonous acids. Zhurnal Obshchei Khimii 1986, 56, 773-781.*
US 6,248,921, 06/2001, Weferling et al. (withdrawn).
PCT International Search Report for PCT/EP2009/007145, mailed Jan. 25, 2010.
English Translation of the PCT International Preliminary Report on Patentability PCT/EP2009/007145 mailed Jun. 30, 2011.
English abstract for JP 05230085, Sep. 7, 1993.
Russian Journal of General Chemistry (translation of Zhurnal Obshchei Khimii), 74(6) pp. 864-872; XP002561442 (2004).
PCT International Search Report for PCT/EP2009/007123, mailed Jan. 29, 2010.
English Translation of the PCT International Preliminary Report on Patentability PCT/EP2009/007123 mailed May 19, 2011.
Montchamp; "Recent advances in phosphorus—carbon bond formation: synthesis of H-phosphinic acid derivatives from hypophosphus compounds" Journal of Organometallic Chemistry Elsevier-Sequoua S.A. Lausanne, CH, vol. 690; pp. 2388-2406; XP004877374 (May 16, 2005).
Sylvine Deprele et al. "Palladium-Catalyzed Hydrophosphinylation of Alkenes and Alkynes;" Journal of the American Chemical Society, American Chemical Society, Washington DC, US vol. 124, No. 32 p. 9387, XP002500862 (Jan. 1, 2002).
Bravo-Altamirano et al.: "A Novel Approach to Phosphinic Acids from Hypophosphorus Acid;" Tetrahedron Letters, Elsevier, Amsterdam, NL vol. 48, No. 33, pp. 5755-5759, XP022163552 (Jul. 19, 2007).
Sylvine Deprele et al.: "Environmentally Benign Synthesis of H-Phosphinic Acids Using a Water Tolerant, Recyclable Polymer-Supported Catalyst;" Organic Letters, American Chemical Society, US, vol. 6, No. 21, pp. 3805-3808 XP002500861 (Jan. 1, 2004).
Patrice Ribiere et al: "NiCL2-Catalyzed Hydrophosphinylation;" Journal of Organic Chemistry, American Chemical Society, Easton, US, vol. 70, No. 10, pp. 4064-4072, XP002530191 (Jan. 1, 2005).
Courdray L. et al.: "Allylic Phosphinates via Pd-Catalyzed Allylation of H-Phosphinic Acids with Allylic Alcohols;" Organic letters, vol. 10, No. 6, pp. 1123-1126 XP002561368 (Feb. 21, 2008).
Mastalerz: Synthesis of some ethylene-(P,P'-Dialkyl)-Diphosphic Acids as new Potential Antimetabolites of Succinic Acid; Roczniki Chemii Ann. Soc. Chim. Polonorum, vol. 38 pp. 61-66 XP 009126234 (1964).
Kurdyumova et al.: "Synthesis of Phosphinic Acids from Hypophosphites I Acrylates as an Unsaturated Component;" Russian Journal of General Chemistry (Translation of Zhurnal Obshchei Khimii (1997), 67(12) pp. 1852-1856 (Apr. 25, 1997).
English abstract of Khairullin et al,"Reaction of chlorides of acids of trivalent phosphorus with conjugated systems I. Reaction of ethylphosphonous dichloride with alpha-beta-unstaturated acids" Zh. Obshch. Khimii. 36, pp. 289-296 (1966), (Caplus printout only).
PCT International search report for PCT/EP2009/007124, mailed Feb. 22, 2010.
PCT International Preliminary Report on Patentability for PCT/EP2009/007124, mailed May 19, 2011.

(56) References Cited

OTHER PUBLICATIONS

Piotr Majewski: "A New Method for the Preparation of Bis(1-hydroxyalkyl)-phosphinic Acids;" Synthesis, vol. 6, pp. 555-557, XP002558292 (1987).
Hung Kuei Lin et al.: "Competitive inhibition of interfacial catalysis by phospholipase A2: differential interaction of inhibitors with the vesicle interface a controlling factor of inhibitor potency" J. Am. Chem. Soc, vol. 115, No. 10, 1993, pp. 3932-3942 XP009126627 (1993).
Kallinowsky G. et al.: "C13 Nuclear Magnetic Resonance Study of Some Phosphinolipids: Assignments and Conformational Studies;" Magnetic Resonance in Chemistry, vol. 27, No. 7, pp. 647-652 XP002558647 (1989).
PCT International Search Report for PCT/EP2009/007125, mailed Feb. 22, 2010.
English translation of PCT International Preliminary Report on Patentability for PCT/EP2009/007125, mailed May 19, 2011.
PCT International search report for PCT/EP2009/007126, mailed Sep. 2, 2010.
English translation of PCT International Preliminary Report on Patentability for PCT/EP2009/007126, mailed May 19, 2011.
Froestl W. et al.: "Phosphinic Acid Analogues of Gaba. 2. Selective, Orally Acitive Gabab Antagonists," Journal of Medicinal Chemistry, American Chemical Society, Washington, US, vol. 38, No. 17, pp. 3313-3331, XP000999491 (Jan. 1, 1995).
PCT International Preliminary Report on Patentability for PCT/EP2009/007127, mailed Jan. 18, 2010.
English translation of PCT International Preliminary Report on Patentability for PCT/EP2009/007127, mailed May 19, 2011.
PCT International Preliminary Report on Patentability for PCT/EP2009/007128, mailed Jan. 27, 2010.
English translation of PCT International Preliminary Report on Patentability for PCT/EP2009/007128, mailed May 19, 2011.
PCT International Preliminary Report on Patentability for PCT/EP2009/007129, mailed Feb. 22, 2010.
English translation of PCT International Preliminary Report on Patentability for PCT/EP2009/007129, mailed May 19, 2011.
PCT International Preliminary Report on Patentability for PCT/EP2009/007130, mailed Apr. 29, 2010.
English translation of PCT International Preliminary Report on Patentability for PCT/EP2009/007130, mailed May 19, 2011.
Nifant'ev et al.: "Reactions of acetylenes with hypophosphorous aand phosphous acids;" Journal of General Chemistry USSR Consultants Bureau, New York, NY, US vol. 56 No. 4 pp. 680-688 XP002165520 (Sep. 20, 1986).
English Abstract for DE 2344332, Mar. 27, 1975, (caplus printout only).
Kabachnik et al.: "Synthesis and properties of some ethylenepiphosphoryl compounds," Russian Chemical Bulletin, vol. 23, No. 10 p. 2205 XP002557075 (1974).
Saratovskikh I. et al.: "Phosphorus-containing Aminocarboxylic Acids: XIV. Synthesis of Analogs of [alpha]-Substituted Glutamic Acid" Russian Journal of General Chemistry Nauka/Interperiodica, Mo, vol. 75, No. 7 pp. 1077-1084 XP019301159 (Jul. 1, 2005).
Chemical Abstracts Service, Columbus, Ohio, US: Gareev et al.: "Stereochemistry of a 1,3-dipolar cycloaddition of diazomethane to alpha-substituted vinylphosphoryl compounds containing a chiral phosphorus atom" XP002567581 (1979), (Caplus printout only).
Chemical Abstracts Service, Columbus, Ohio, US: Raevskii et al. "Electron-donor and acceptor functions of physiologically active and model compounds. V. Calculation of the electron-donor function of phosphoryl oxygen" XP002567582 (1984), (caplus printout only).
Isabelle Abrunhosa Thomas et al.: "Alkylation of H—Phosphinate Esters under Basic Conditions;" Jounal of Organic Chemistry, American Chemical Society, Easton,; US, vol. 72, No. 8 pp. 2851-2856 XP002530192 (Jan. 1, 2007).
Catherine Ruflin et al.: "Tetrakis(trimethylsilyl)hypophosphate P202(OTMS)4: Synthesis, reactivity and application as flame retardants;" Heteroatom Chemistry, VCH publishers, Defield Beach, FL, US, vol. 18, No. 7 pp. 721-731 XP009118331 (Nov. 6, 2007).

PCT International Search Report for PCT/EP2009/007131, mailed Feb. 8, 2010.
English translation of the PCT International Preliminary Report on Patentability for PCT/EP2009/007131, mailed May 19, 2011.
PCT International Preliminary Report on Patentability for PCT/EP2009/007132, mailed Feb. 15, 2010.
English translation of PCT International Preliminary Report on Patentability for PCT/EP2009/007132, mailed May 19, 2011.
PCT International Preliminary Report on Patentability for PCT/EP2009/007133, mailed Feb. 3, 2010.
English translation of PCT International Preliminary Report on Patentability for PCT/EP2009/007133, mailed May 19, 2011.
Database Beilstein [Online] Beilstein Institute for Organic Chemistry, Frankfurt-Main, DE; XP002561148, retrived from xfire Database accession No. Reaction ID 198358, abstract (1954).
PCT International Preliminary Report on Patentability for PCT/EP2009/007134, mailed Feb. 18, 2010.
English translation of PCT International Preliminary Report on Patentability for PCT/EP2009/007134, mailed May 19, 2011.
PCT International Preliminary Report on Patentability for PCT/EP2009/007135, mailed Mar. 17, 2010.
English translation of PCT International Preliminary Report on Patentability for PCT/EP2009/007135, mailed May 26, 2011.
Bravo-Altamirano et al.: "Palladium-Catalyzed Reaction of Hypophosphorous Compounds with Allenes, Dienes, and Allylic Electrophiles: Methodology for the Synthesis of Allylic H—Phosphinates" J. Org. Chem., vol. 73, No. 6, pp. 2292-2301 XP002567417 (Feb. 15, 2008).
Nadia Valiaeva et al.: "Phosophinic Acid Pseudopeptides Analogous to Glutamyl-gamma-glutamate: Synthesis and Coupling to Pteroyl Azides Leads to Potent Inhibitors of Folypoly-gamma-glutamate Synthetase;" J. Or. Chem., vol. 66, pp. 5146-5154 XP002567418 (2001).
Yamagishi takehiro et al.: "Stereoselective Synthesis of beta-Amino-alpha-hydroxy(allyl)phosphinates and an Application to the Synthesis of a Building Block with Phosphinyl Peptides" Synlett, No. 9, pp. 1471-1474, XP 002567142 (Jan. 1, 2002).
PCT International Search Report for PCT/EP2009/007136, mailed Mar. 22, 2010.
English translation of the PCT International Preliminary Report on Patentability for PCT/EP2009/007136, mailed Jun. 16, 2011.
Database Beilstein [online] Beilstein Institute for Organic Chemistry, Frankfurt-Main, DE; Database accession No. Reaction ID 101395 XP 002567148 (1956).
PCT International Search Report for PCT/EP2009/007137, mailed Mar. 12, 2010.
English translation of the PCT International Preliminary Report on Patentability for PCT/EP2009/007137, mailed Jun. 16, 2011.
Yamagishi et al.: "Diastereoselective synthesis of beta-substituted alpha-hydroxyphosphinates through hydrophosphinylation of alpha-heteroatom-substituted aldehydes;" Tetrahedron, Elsevier Science Publishers, Amsterdam, NL., vol. 59, No. 6 pp. 767-772 XP004404933 (Feb. 3, 2003).
Database Beilstein [online] Beilstein Institute for Organic Chemistry, Frankfurt-Main, DE; Database accession No. Reaction ID 970178 XP 002571550 (1963).
PCT International Search Report for PCT/EP2009/007139, mailed Mar. 22, 2010.
English translation of the PCT International Preliminary Report on Patentability for PCT/EP2009/007139, mailed Jun. 30, 2011.
PCT International Search Report for PCT/EP2009/007140, mailed Mar. 11, 2010.
English translation of the PCT International Preliminary Report on Patentability for PCT/EP2009/007140, mailed Jun. 30, 2011.
PCT International Search Report for PCT/EP2009/008964, mailed Jul. 9, 2010.
English translation of the PCT International Preliminary Report on Patentability for PCT/EP2009/008964, mailed Jun. 30, 2011.
Alonso et al.: "Transition-Metal Catalyzed Addition of Heteroatom-Hydrogen Bonds to Alkynes;" Chem. Rev., pp. 3148-3153 XP002556525 (2004).

(56) References Cited

OTHER PUBLICATIONS

Pudovick et al.: "Free Radical Reaction of Addition of Partial Esters of Phosphorus Acids to Acetylenic Hydrocarbons;" J. Gen. Chem. USSR, vol. 39, No. 5, pp. 986-988 XP009126232 (1969).
Database Beilstein [online] Beilstein Institute for Organic Chemistry, Frankfurt-Main, DE; Database accession No. Reaction BRN 3110535, retrieved from xfire XP002557076 (1967).
Database Beilstein [Online] Beilstein Institute for Organic Chemistry, Frankfurt-Main, DE; Database accession No. Reaction BRN 8075738 XP 002557077 (1997).
PCT International Search Report for PCT/EP2009/007142, mailed Feb. 9, 2010.
English translation of PCT International Preliminary Report on Patentability for PCT/EP2009/007142, mailed Jun. 30, 2011.
English Abstract for SU 314758, Sep. 21, 1971, (Caplus printout only).
Yamagishi et al.: "Lipase-catalyzed kinetic resolution of alpha-hydroxy-H-phosphinates" Tetrahedron Letters, Elsevier, Amsterdam, NL, vol. 45, No. 36, pp. 6713-6716 XP004556626 (Aug. 30, 2004).
Anderson et al.: "Antidiabetic agents: a new class of reversible carnitine palmitoyltrasferase I inhibitors;" J. Med. Chem., vol. 38, No. 18, pp. 3448-3450 XP002564326 (1995).
Karanewsky et al.: "Synthesis of Phosphinic Monoesters from Phosphonous Acids" Tetrahedron Letters, Elsevier, Amsterdam, NL, vol. 27, No. 16, pp. 1751-1754 XP001084930 (Jan. 1, 1986).
PCT International Search Report for PCT/EP2009/007143, mailed Feb. 17, 2010.
English translation of the PCT International Preliminary Report on Patentability for PCT/EP2009/007143, mailed Jun. 30, 2011.
Rezanka et al.: "Synthesis of a Bifunctional Monophosphinate DOTA Derivative Having a Free Carboxylate Group in the Phosphorus Side Chain;" Synthesis, Georg Thieme Verlag, Stuttgart pp. 1431-1435 XP009126087 (Sep. 1, 2008).
Database Beilstein [online] Beilstein Institute for Organic Chemistry, Frankfurt-Main, DE; Database accession No. Reaction ID 938840 XP002557780 (1962).
Kielbasinski et al: "Enzymatic reactions in ionic liquids: lipase-catalysed kinetic resolution of racemic, P-chiral hydroxymethanephosphinates and hydroxmethylphosphine oxides;" Tetrahedron Asymmetry, Pergamon Press Ltd, Oxford, GB, vol. 13, No. 7, pp. 735-738 XP004354866 (May 2, 2002).
Maier: "Organic Phosphorus compounds 91.1 Synthesis and Properties of 1-Amino-2-Arylethylphosphinic and -Phosphinic Acids as well as Phosphine Oxides;" Phosphorus, Sulfur and Silicon and the Related Elements, Gordon and Breach Science Publishers, Amsterdam, GB, vol. 53, No. 1/04 pp. 43-67 XP000671624 (Jan. 1, 1990).
English Translation of Houben-Weyl, vol. 1211, pp. 258-259 (Apr. 22, 1963).
English Translation of Houben-Weyl, vol. 1211, p. 306 (Apr. 22, 1963).
English Translation of Sasse K ED—Sasse K: "Houben-Weyl Methoden der Organischen Chemie", Organische Phosphor-Verbindungen; [Methoden der Organischen Chemie], Stuttgart, G. Thieme Verlag DE, XP002500739, pp. 257-259, 261, 294-301 (Jan. 1, 1963).
English Translation of "1" In: Sasse K ED—Sasse K: "Houben-Weyl Methoden der Organischen Chemie;" Organische Phosphor-Verbindungen; [Methoden der Organischen Chemie], Stuttgart, G. Thieme Verlag, DE. pp. 358, XP002564325 (Jan. 1, 1963).
English Translation of Regitz:"Houben-Weyl Methoden der Organischen Chemie" Organische Phosphor-Verbindungen; [Methoden der Organischen Chemie], Stuggart, G. Thieme Verlag, DE, pp. 308-309 XP002564334 (Jan. 1, 1982).
English Translation of Issleib, et al.: "Synthese und Reaktionsverhalten der Athylen-bis-organophosphine;" Chemische Berichte, vol. 101, pp. 2197-2202 XP009126251 (1968).
English Translation of Regitz: "Houben-Weyl Methoden der Organischen Chemie" p. 188, (Jan. 1, 1982).
English translation of Diel et al.: "Organische Phosphorverbindungen 84. Herstellung Eigenschaften und Biologische Wirkung von Hydrazino-Methyl-Phosphon-und Phosphinsaeuren und Derivatin;" Phosphorus and Sulfur and the Related Elements, Gordon and Breach—Harwood Academic, CH, vol. 36, pp. 85-98 XP001105809 (Jan. 1, 1998).
English Translation of Sasse K ED—Sasse K: "Houben-Weyl Methoden der Organischen Chemie", Organische Phosphor-Verbindungen; [Methoden der Organischen Chemie], Stuttgart, G. Thieme Verlag DE, XP002557781, pp. 228-229 (Jan. 1, 1963).
English Abstract for DE 2344332, Mar. 27, 1975.

* cited by examiner

PROCESS FOR PREPARING ETHYLENEDIALKYLPHOSPHINIC ACIDS, ESTERS AND SALTS BY MEANS OF ACETYLENE AND USE THEREOF

The invention relates to a process for preparing ethylenedialkylphosphinic acids, esters and salts by means of acetylene and to the use thereof.

Ethylenediphosphinic acids are known in principle from the prior art. For instance, DE-A-199 12 920 and WO-A-0 157 050 describe phosphinic acids of the H—P(O)(OX)—[CH$_2$CH$_2$—P(O)(OX)]$_n$H type where X is H, metal or an alkyl group and n is greater than 1. These phosphinic acids are oligomeric or polymeric. They are prepared by processes which give telomers but do not permit controlled access to phosphinic acids with specific chain length.

Organic phosphinic acids and salts and esters thereof are known as flame retardants. For instance, EP 0 699 708 A1 describes flame-retardant polyester molding materials, wherein the polyester molding materials are rendered flame-retardant by the addition of calcium or aluminum salts of phosphinic or diphosphinic acids. The aforementioned salts are obtained by reacting the appropriate phosphinic acids with calcium hydroxide or aluminum hydroxide.

Owing to their high phosphorus content and their bidentate nature, the diphosphinic acids are described as being very effective reactive flame retardants for polyesters, for example for textile applications. This is particularly true of ethylenebis(methylphosphinic acid), especially in the form of the glycol ester thereof (DE 22 36 037 A1).

The preparation of ethylenebis(methylphosphinic acid) is technically very complex and is effected, for example, by an Arbuzov reaction of diisopropyl methylphosphonite, prepared from methylphosphonous dichloride by reaction with alcohols, with ethylene bromide [P. Mastalerz, Rocziniki Chem 38 (1964), pages 61-64] and subsequent ester cleavage.

DE 23 02 523 A1 describes the reaction of alkylphosphonous esters with ethyne(acetylene) and the subsequent cleavage of the diester formed with HCl to form alkyl chlorides. The alkylphosphonous esters used here too are prepared from the corresponding phosphonous dihalides.

One disadvantage of the aforementioned processes is that they include the technically difficult cleavage of the corresponding esters as the last step, and can therefore be performed only with great difficulty. In addition, halogenated by-products are formed, which, like some of the aforementioned starting materials themselves too, are toxic, self-igniting and/or corrosive, i.e. are highly undesirable.

There has to date been a lack of processes for preparing ethylenedialkyl-phosphinic acids, esters and salts which are amenable to economically viable use on the industrial scale and which especially enable a high space-time yield. There is also a lack of processes which are sufficiently effective without troublesome halogen compounds as reactants, and additionally of those in which the end products can be obtained and isolated readily, or else can be prepared in a controlled and desirable manner under controlled reaction conditions (for instance of a transesterification).

This object is achieved by a process for preparing ethylenedialkylphosphinic acids, esters and salts, which comprises a) reacting a phosphinic acid source (I)

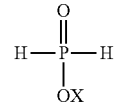

(I)

with olefins IV

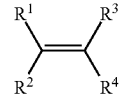

(IV)

in the presence of a catalyst A to give an alkylphosphonous acid (II), or salt or ester thereof,

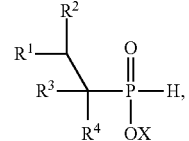

(II)

b) reacting the alkylphosphonous acid (II), or salt or ester thereof, thus formed with an acetylenic compound (V)

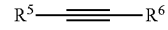

(V)

in the presence of a catalyst B to give the ethylenedialkylphosphinic acid derivative (III)

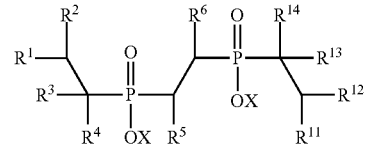

(III)

where $R^1$, $R^2$, $R^3$, $R^4$, $R^5$, $R^6$, $R^{11}$, $R^{12}$, $R^{13}$, $R^{14}$ are the same or different and are each independently H, $C_1$-$C_{18}$-alkyl, $C_6$-$C_{18}$-aryl, $C_6$-$C_{18}$-aralkyl, $C_6$-$C_{18}$-alkylaryl, CN, CHO, OC(O)CH$_2$CN, CH(OH)C$_2$H$_5$, CH$_2$CH(OH)CH$_3$, 9-anthracene, 2-pyrrolidone, (CH$_2$)$_m$OH, (CH$_2$)$_m$NH$_2$, (CH$_2$)$_m$NCS, (CH$_2$)$_m$NC(S)NH$_2$, (CH$_2$)$_m$SH, (CH$_2$)$_m$S-2-thiazoline, (CH$_2$)$_m$SiMe$_3$, C(O)R$^7$, (CH$_2$)$_m$C(O)R$^7$, CH=CH—R$^7$, CH=CH—C(O)R$^7$, and where R$^7$ is $C_1$-$C_8$-alkyl or $C_6$-$C_{18}$-aryl, and m is an integer from 0 to 10, and X is H, $C_1$-$C_{18}$-alkyl, $C_6$-$C_{18}$-aryl, $C_6$-$C_{18}$-aralkyl, $C_6$-$C_{18}$-alkylaryl, (CH$_2$)$_k$OH, CH$_2$—CHOH—CH$_2$OH, (CH$_2$)$_k$O(CH$_2$)$_k$H, (CH$_2$)$_k$—CH(OH)—(CH$_2$)$_k$H, (CH$_2$—CH$_2$O)$_k$H, (CH$_2$—C[CH$_3$]HO)$_k$H, (CH$_2$—C[CH$_3$]HO)$_k$(CH$_2$—CH$_2$O)$_k$H, (CH$_2$—CH$_2$O)$_k$(CH$_2$—C[CH$_3$]HO)H, (CH$_2$—CH$_2$O)$_k$-alkyl, (CH$_2$—C[CH$_3$]HO)$_k$-alkyl, (CH$_2$—C[CH$_3$]HO)$_k$(CH$_2$—CH$_2$O)$_k$-alkyl, (CH$_2$—CH$_2$O)$_k$(CH$_2$—C[CH$_3$]HO)O-alkyl, (CH$_2$)$_k$—CH=CH(CH$_2$)$_k$H, (CH$_2$)$_k$NH$_2$, (CH$_2$)$_k$N[(CH$_2$)$_k$H]$_2$, where k is an integer from 0 to 10, and/or is Mg, Ca, Al, Sb, Sn, Ge, Ti, Fe, Zr, Zn, Ce, Bi, Sr, Mn, Cu, Ni, Li, Na, K, H, and/or is a protonated nitrogen base, and the catalyst A comprises transition metals and/or transition metal compounds and/or catalyst systems composed of a transition metal and/or a transition metal compound and at least one ligand, and the catalyst B comprises peroxide-forming compounds and/or peroxo compounds and/or azo compounds.

Preferably, the ethylenedialkylphosphinic acid (III), or salt or ester thereof, obtained after step b) is subsequently reacted, in a step c), with metal compounds of Mg, Ca, Al, Sb, Sn, Ge, Ti, Fe, Zr, Zn, Ce, Bi, Sr, Mn, Li, Na, K and/or a protonated nitrogen base to give the corresponding ethylenedialkylphosphinic salts (III) of these metals and/or a nitrogen compound.

Preferably, the alkylphosphonous acid (II), or salt or ester thereof, obtained after step a) and/or the ethylenedialkylphosphinic acid (III), or salt or ester thereof, obtained after step b) and/or the reaction solution thereof which results in each case is esterified with an alkylene oxide or an alcohol M-OH and/or M'-OH, and the alkylphosphonous ester (II) and/or ethylenedialkylphosphinic ester (III) formed in each case is subjected to the further reaction steps b) or c).

Preferably, the $C_6$-$C_{18}$-aryl, $C_6$-$C_{18}$-aralkyl and $C_6$-$C_{18}$-alkylaryl groups have substitution by $SO_3X_2$, —$C(O)CH_3$, OH, $CH_2OH$, $CH_3SO_3X_2$, $PO_3X_2$, $NH_2$, $NO_2$, $OCH_3$, SH and/or $OC(O)CH_3$.

Preferably, $R^1$, $R^2$, $R^3$, $R^4$, $R^5$, $R^6$, $R^{11}$, $R^{12}$, $R^{13}$, $R^{14}$ are the same or different and are each independently H, methyl, ethyl, n-propyl, isopropyl, n-butyl, isobutyl, tert-butyl and/or phenyl.

Preferably, X is H, Ca, Mg, Al, Zn, Ti, Fe, Ce, methyl, ethyl, n-propyl, isopropyl, n-butyl, isobutyl, tert-butyl, phenyl, ethylene glycol, propyl glycol, butyl glycol, pentyl glycol, hexyl glycol, allyl and/or glycerol.

Preferably, m=1 to 10 and k=2 to 10.

Preferably, the catalyst system A is formed by reaction of a transition metal and/or a transition metal compound and at least one ligand.

Preferably, the transition metals and/or transition metal compounds are those from the seventh and eighth transition groups.

Preferably, the transition metals and/or transition metal compounds are rhodium, nickel, palladium, ruthenium and/or platinum.

Preferably, the catalyst B is hydrogen peroxide, sodium peroxide, lithium peroxide, potassium persulfate, sodium persulfate, ammonium persulfate, sodium peroxodisulfate, potassium peroxoborate, peracetic acid, benzoyl peroxide, di-t-butyl peroxide and/or peroxodisulfuric acid and/or azodiisobutyronitrile, 2,2'-azobis(2-amidinopropane)dihydrochloride and/or 2,2'-azobis(N,N'-dimethyleneisobutyramidine)dihydrochloride.

Preferably, the acetylenic compound (V) is acetylene, methylacetylene, 1-butyne, 1-hexyne, 2-hexyne, 1-octyne, 4-octyne, 1-butyn-4-ol, 2-butyn-1-ol, 3-butyn-1-ol, 5-hexyn-1-ol, 1-octyn-3-ol, 1-pentyne, phenylacetylene and/or trimethylsilylacetylene.

Preferably, the alcohol of the general formula M-OH comprises linear or branched, saturated and unsaturated, monohydric organic alcohols having a carbon chain length of $C_1$-$C_{18}$, and the alcohol of the general formula M'-OH comprises linear or branched, saturated and unsaturated, polyhydric organic alcohols having a carbon chain length of $C_1$-$C_{18}$.

The invention also relates to the use of ethylenedialkylphosphinic acids, esters and salts prepared according to one or more of claims 1, 3, 7 and 8 as an intermediate for further syntheses, as a binder, as a crosslinker or accelerator in the curing of epoxy resins, polyurethanes and unsaturated polyester resins, as polymer stabilizers, as crop protection agents, as a therapeutic or additive in therapeutic compositions for humans and animals, as a sequestrant, as a mineral oil additive, as an anticorrosive, in washing and cleaning composition applications and in electronics applications.

The invention likewise relates to the use of ethylenedialkylphosphinic acids, salts and esters (III) which have been prepared according to one or more of claims 1, 3, 7 and 8 as flame retardants, especially flame retardants for clearcoats and intumescent coatings, flame retardants for wood and other cellulosic products, as a reactive and/or nonreactive flame retardant for polymers, for production of flame-retardant polymer molding materials, for production of flame-retardant polymer moldings, and/or for rendering pure and blended polyester and cellulose fabrics flame-retardant by impregnation.

The invention also relates to a flame-retardant thermoplastic or thermoset polymer molding material comprising 0.5 to 45% by weight of ethylenedialkylphosphinic acids, salts or esters (III) which have been prepared according to one or more of claims 1, 3, 7 and 8, 0.5 to 99% by weight of thermoplastic or thermoset polymer or mixtures thereof, 0 to 55% by weight of additives and 0 to 55% by weight of filler or reinforcing materials, where the sum of the components is 100% by weight.

Finally, the invention additionally relates to flame-retardant thermoplastic or thermoset polymer moldings, films, filaments and fibers, comprising 0.5 to 45% by weight of ethylenedialkylphosphinic acids, salts or esters (III) which have been prepared according to one or more of claims 1, 3, 7 and 8, 0.5 to 99% by weight of thermoplastic or thermoset polymer or mixtures thereof, 0 to 55% by weight of additives and 0 to 55% by weight of filler or reinforcing materials, where the sum of the components is 100% by weight.

All aforementioned reactions may also be performed stepwise; equally, it is also possible in the different process steps to use the particular resulting reaction solutions.

Preferably, $R^{11}$=$R^1$, $R^{12}$=$R^2$, $R^{13}$=$R^3$ and $R^{14}$=$R^4$.

When the ethylenedialkylphosphinic acid (III) after step c) is an ester, it is possible with preference to perform an acidic or basic hydrolysis in order to obtain the free ethylenedialkylphosphinic acid or salt thereof.

Preferably, m is 1 to 10 and k is 2 to 10.

Preferably, the ethylenedialkylphosphinic acid is ethylenebis(ethylphosphinic acid), ethylenebis(propylphosphinic acid), ethylenebis(i-propylphosphinic acid), ethylenebis(butylphosphinic acid), ethylenebis(sec-propylphosphinic acid), ethylenebis(i-propylphosphinic acid), ethylenebis(i-butylphosphinic acid), ethylenebis(2-phenylethylphosphinic acid).

Preferably, the ethylenedialkylphosphinic ester is a propionic acid, methyl, ethyl; i-propyl; butyl, phenyl; 2-hydroxyethyl, 2-hydroxypropyl, 3-hydroxypropyl, 4-hydroxybutyl and/or 2,3-dihydroxypropyl ester of the abovementioned ethylenedialkylphosphinic acids.

Preferably, the ethylenedialkylphosphinic salt is an aluminum(III), calcium(II), magnesium(II), cerium(III), Ti(IV) and/or zinc(II) salt of the abovementioned ethylenedialkylphosphinic acids.

Preferably, the transition metals for catalyst A comprise elements of the seventh and eighth transition groups (in modern nomenclature, a metal of group 7, 8, 9 or 10), for example rhenium, ruthenium, cobalt, rhodium, iridium, nickel, palladium and platinum.

Preferred sources of the transition metals and transition metal compounds are their metal salts. Suitable salts are those of mineral acids containing the anions fluoride, chloride, bromide, iodide, fluorate, chlorate, bromate, iodate, fluorite, chlorite, bromite, iodite, hypofluorite, hypochlorite, hypobromite, hypoiodite, perfluorate, perchlorate, perbromate, periodate, cyanide, cyanate, nitrate, nitride, nitrite, oxide, hydroxide, borate, sulfate, sulfite, sulfide, persulfate, thiosulfate, sulfamate, phosphate, phosphite, hypophosphite, phosphide, carbonate and sulfonate, for example methanesulfonate, chlorosulfonate, fluorosulfonate, trifluoromethanesulfonate, benzenesulfonate, naphthylsulfonate, toluenesulfonate, t-butylsulfonate, 2-hydroxypropanesulfonate and sulfonated ion exchange resins; and/or organic salts, for example acetylacetonates and salts of a carboxylic acid having up to 20 carbon atoms, for example formate, acetate, propionate, butyrate, oxalate, stearate and citrate including halogenated carboxylic acids having up to 20 carbon atoms, for instance trifluoroacetate, trichloroacetate.

A further source of the transition metals and transition metal compounds is salts of the transition metals with tetraphenylborate and halogenated tetraphenylborate anions, for example perfluorophenylborate.

Suitable salts similarly include double salts and complex salts consisting of one or more transition metal ions and independently one or more alkali metal, alkaline earth metal, ammonium, organic ammonium, phosphonium and organic phosphonium ions and independently one or more of the abovementioned anions. Examples of suitable double salts are ammonium hexachloropalladate and ammonium tetrachloropalladate.

Preferred sources of the transition metals are the transition metal as an element and/or a transition metal compound in its zero-valent state.

Preferably, the transition metal is used in metallic form, or as an alloy with further metals, in which case boron, zirconium, tantalum, tungsten, rhenium, cobalt, iridium, nickel, palladium, platinum and/or gold is preferred here. The transition metal content in the alloy used is preferably 45-99.95% by weight.

Preferably, the transition metal is used in microdisperse form (particle size 0.1 mm-100 μm).

Preferably, the transition metal is used supported on a metal oxide, for instance alumina, silica, titanium dioxide, zirconium dioxide, zinc oxide, nickel oxide, vanadium oxide, chromium oxide, magnesium oxide, Celite®, kieselguhr, on a metal carbonate, for instance barium carbonate, calcium carbonate, strontium carbonate, on a metal sulfate, for instance barium sulfate, calcium sulfate, strontium sulfate, on a metal phosphate, for instance aluminum phosphate, vanadium phosphate, on a metal carbide, for instance silicone carbide, on a metal aluminate, for instance calcium aluminate, on a metal silicate, for instance aluminum silicate, chalks, zeolites, bentonite, montmorillonite, hectorite, on functionalized silicates, functionalized silica gels, for instance SiliaBond®, QuadraSil™, on functionalized polysiloxanes, for instance Deloxan®, on a metal nitride, on carbon, activated carbon, mullite, bauxite, antimonite, scheelite, perovskite, hydrotalcite, heteropolyanions, on functionalized and unfunctionalized cellulose, chitosan, keratin, heteropolyanions, on ion exchangers, for instance Amberlite™, Amberjet™, Ambersep™, Dowex®, Lewatit®, ScavNet®, on functionalized polymers, for instance Chelex®, QuadraPure™, Smopex®, PolyOrgs®, on polymer-bound phosphines, phosphine oxides, phosphinates, phosphonates, phosphates, amines, ammonium salts, amides, thioamides, ureas, thioureas, triazines, imidazoles, pyrazoles, pyridines, pyrimidines, pyrazines, thiols, thiol ethers, thiol esters, alcohols, alkoxides, ethers, esters, carboxylic acids, acetates, acetals, peptides, hetarenes, polyethyleneimine/silica and/or dendrimers.

Suitable sources for the metal salts and/or transition metals likewise preferably include their complex compounds. Complex compounds of the metal salts and/or transition metals are composed of the metal salts/transition metals and one or more complexing agents. Suitable complexing agents include for example olefins, diolefins, nitriles, dinitriles, carbon monoxide, phosphines, diphosphines, phosphites, diphosphites, dibenzylideneacetone, cyclopentadienyl, indenyl or styrene. Suitable complex compounds of the metal salts and/or transition metals may be supported on the abovementioned support materials.

The proportion in which the supported transition metals mentioned are present is preferably in the range from 0.01% to 20% by weight, more preferably from 0.1% to 10% by weight and even more preferably from 0.2% to 5% by weight, based on the total mass of the support material.

Suitable sources for transition metals and transition metal compounds include for example palladium, platinum, nickel, rhodium; palladium, platinum, nickel or rhodium, on alumina, on silica, on barium carbonate, on barium sulfate, on calcium carbonate, on strontium carbonate, on carbon, on activated carbon; platinum-palladium-gold alloy, aluminum-nickel alloy, iron-nickel alloy, lanthanoid-nickel alloy, zirconium-nickel alloy, platinum-iridium alloy, platinum-rhodium alloy; Raney® nickel, nickel-zinc-iron oxide; palladium(II) chloride, palladium(II) bromide, palladium(II) iodide, palladium(II) fluoride, palladium(II) hydride, palladium(II) oxide, palladium(II) peroxide, palladium(II) cyanide, palladium(II) sulfate, palladium(II) nitrate, palladium(II) phosphide, palladium(II) boride, palladium(II) chromium oxide, palladium (II) cobalt oxide, palladium(II) carbonate hydroxide, palladium(II) cyclohexane butyrate, palladium(II) hydroxide, palladium(II) molybdate, palladium(II) octanoate, palladium (II) oxalate, palladium(II) perchlorate, palladium(II) phthalocyanine, palladium(II) 5,9,14,18,23,27,32,36-octabutoxy-2,3-naphthalocyanine, palladium(II) sulfamate, palladium (II) perchlorate, palladium(II) thiocyanate, palladium(II) bis (2,2,6,6-tetramethyl-3,5-heptanedionate), palladium(II) propionate, palladium(II) acetate, palladium(II) stearate, palladium(II) 2-ethylhexanoate, palladium(II) acetylacetonate, palladium(II) hexafluoro-acetylacetonate, palladium(II) tetrafluoroborate, palladium(II) thiosulfate, palladium(II) trifluoroacetate, palladium(II) phthalocyaninetetrasulfonic acid tetrasodium salt, palladium(II) methyl, palladium(II) cyclopentadienyl, palladium(II) methylcyclopentadienyl, palladium(II) ethylcyclopentadienyl, palladium(II) pentamethylcyclopentadienyl, palladium(II) 2,3,7,8,12,13,17,18-octaethyl-21H,23H-porphine, palladium(II) 5,10,15,20-tetraphenyl-21H,23H-porphine, palladium(II) bis(5-[[4-(dimethylamino)phenyl]imino]-8(5H)-quinolinone), palladium(II) 2,11,20,29-tetra-tert-butyl-2,3-naphthalocyanine, palladium(II) 2,9,16,23-tetraphenoxy-29H,31H-phthalocyanine, palladium(II) 5,10,15,20-tetrakis(pentafluorophenyl)-21H,23H-porphine and the 1,4-bis-(diphenylphosphine) butane, 1,3-bis(diphenylphosphino)propane, 2-(2'-di-tert-butylphosphine)biphenyl, acetonitrile, benzonitrile, ethylenediamine, chloroform, 1,2-bis(phenylsulfinyl)ethane, 1,3-bis(2,6-diisopropylphenyl)imidazolidene)(3-chloropyridyl), 2'-(dimethylamino)-2-biphenylyl, dinorbornylphosphine, 2-(dimethylaminomethyl)ferrocene, allyl, bis(diphenylphosphino)butane, (N-succinimidyl)bis (triphenylphosphine), dimethylphenylphosphine, methyldiphenylphosphine, 1,10-phenanthroline, 1,5-cyclooctadiene, N,N,N',N'-tetramethylethylenediamine, triphenylphosphine, tri-o-tolylphosphine, tricyclohexylphosphine, tributylphosphine, triethylphosphine, 2,2'-bis(diphenylphosphino)-1,1'-binaphthyl, 1,3-bis(2,6-diisopropylphenyl)-imidazol-2-ylidene, 1,3-bis(mesityl)imidazol-2-ylidene, 1,1'-bis(diphenyl-phosphino)ferrocene, 1,2-bis(diphenylphosphino)ethane, N-methylimidazole, 2,2'-bipyridine, (bicyclo[2.2.1]hepta-2,5-diene), bis(di-tert-butyl(4-dimethyl-aminophenyl)phosphine), bis(tert-butyl isocyanide), 2-methoxyethyl ether, ethylene glycol dimethyl ether, 1,2-dimethoxyethane, bis(1,3-diamino-2-propanol), bis(N,N-diethylethylenediamine), 1,2-diaminocyclohexane, pyridine, 2,2':6',2"-terpyridine, diethyl sulfide, ethylene and amine complexes thereof; nickel(II) chloride, nickel(II) bromide, nickel(II) iodide, nickel(II) fluoride, nickel(II) hydride, nickel(II) oxide, nickel(II) peroxide, nickel(II) cyanide, nickel(II) sulfate, nickel(II) nitrate, nickel(II) phosphide, nickel(II) boride, nickel(II) chromium oxide, nickel(II) cobalt oxide, nickel(II) carbonate hydroxide, nickel(II) cyclohexane butyrate, nickel(II) hydroxide, nickel(II) molybdate, nickel(II) octanoate, nickel(II) oxalate, nickel(II) perchlorate, nickel(II) phthalocyanine, nickel(II) 5,9,14,18,23,27,32,36-octabutoxy-2,3-naphthalocyanine, nickel(II) sulfamate, nickel(II) perchlorate, nickel(II) thiocyanate, nickel(II) bis(2,2,6,6-tetramethyl-3,5-heptanedionate), nickel(II) propionate, nickel(II) acetate, nickel(II) stearate, nickel(II) 2-ethylhexanoate, nickel(II) acetylacetonate, nickel(II) hexafluoroacetylacetonate, nickel(II) tetrafluoroborate, nickel(II) thiosulfate, nickel(II) trifluoroacetate, nickel(II) phthalocyaninetetrasulfonic acid tetrasodium salt, nickel(II) methyl, nickel(II) cyclopentadienyl, nickel(II) methylcyclopentadienyl, nickel(II) ethylcyclopentadienyl, nickel(II) pentamethylcyclopentadienyl, nickel(II) 2,3,7,8,12,13,17,18-octaethyl-21H,23H-porphine, nickel(II) 5,10,15,20-tetraphenyl-21H,23H-porphine, nickel(II) bis(5-[[4-(dimethylamino)phenyl]imino]-8(5H)-quinolinone), nickel(II) 2,11,20,29-tetra-tert-butyl-2,3-naphthalocyanine, nickel(II) 2,9,16,23-tetraphenoxy-29H,31H-phthalocyanine, nickel(II) 5,10,15,20-tetrakis(pentafluorophenyl)-21H,23H-porphine and the 1,4-bis-(diphenylphosphine)butane, 1,3-bis(diphenylphosphino)propane, 2-(2'-di-tert-butylphosphine)biphenyl, acetonitrile, benzonitrile, ethylenediamine, chloroform, 1,2-bis(phenylsulfinyl)ethane, 1,3-bis(2,6-diisopropylphenyl)imidazolidene)(3-chloropyridyl), 2'-(dimethylamino)-2-biphenylyl, dinorbornylphosphine, 2-(dimethylaminomethyl)ferrocene, allyl, bis(diphenylphosphino)butane, (N-succinimidyl)bis(triphenylphosphine), dimethylphenylphosphine, methyldiphenylphosphine, 1,10-phenanthroline, 1,5-cyclooctadiene, N,N,N',N'-tetramethylethylenediamine, triphenylphosphine, tri-o-tolylphosphine, tricyclohexylphosphine, tributylphosphine, triethylphosphine, 2,2'-bis(diphenylphosphino)-1,1'-binaphthyl, 1,3-bis(2,6-diisopropylphenyl)-imidazol-2-ylidene, 1,3-bis(mesityl)imidazol-2-ylidene, 1,1'-bis(diphenyl-phosphino)ferrocene, 1,2-bis(diphenylphosphino)ethane, N-methylimidazole, 2,2'-bipyridine, (bicyclo[2.2.1]hepta-2,5-diene), bis(di-tert-butyl(4-dimethyl-aminophenyl)phosphine), bis(tert-butyl isocyanide), 2-methoxyethyl ether, ethylene glycol dimethyl ether, 1,2-dimethoxyethane, bis(1,3-diamino-2-propanol), bis(N,N-diethylethylenediamine), 1,2-diaminocyclohexane, pyridine, 2,2':6',2"-terpyridine, diethyl sulfide, ethylene and amine complexes thereof; platinum(II) chloride, platinum(II) bromide, platinum(II) iodide, platinum(II) fluoride, platinum(II) hydride, platinum(II) oxide, platinum(II) peroxide, platinum(II) cyanide, platinum(II) sulfate, platinum(II) nitrate, platinum(II) phosphide, platinum(II) boride, platinum(II) chromium oxide, platinum(II) cobalt oxide, platinum(II) carbonate hydroxide, platinum(II) cyclohexane butyrate, platinum(II) hydroxide, platinum(II) molybdate, platinum(II) octanoate, platinum(II) oxalate, platinum(II) perchlorate, platinum(II) phthalocyanine, platinum(II) 5,9,14,18,23,27,32,36-octabutoxy-2,3-naphthalocyanine, platinum(II) sulfamate, platinum(II) perchlorate, platinum(II) thiocyanate, platinum(II) bis(2,2,6,6-tetramethyl-3,5-heptanedionate), platinum(II) propionate, platinum(II) acetate, platinum(II) stearate, platinum(II) 2-ethylhexanoate, platinum(II) acetylacetonate, platinum(II) hexafluoroacetyl-acetonate, platinum(II) tetrafluoroborate, platinum(II) thiosulfate, platinum(II) trifluoroacetate, platinum(II) phthalocyaninetetrasulfonic acid tetrasodium salt, platinum(II) methyl, platinum(II) cyclopentadienyl, platinum(II) methylcyclo-pentadienyl, platinum(II) ethylcyclopentadienyl, platinum(II) pentamethyl-cyclopentadienyl, platinum(II) 2,3,7,8,12,13,17,18-octaethyl-21H,23H-porphine, platinum(II) 5,10,15,20-tetraphenyl-21H,23H-porphine, platinum(II) bis(5-[[4-(dimethylamino)phenyl]imino]-8(5H)-quinolinone), platinum(II) 2,11,20,29-tetra-tert-butyl-2,3-naphthalocyanine, platinum(II) 2,9,16,23-tetraphenoxy-29H,31H-phthalocyanine, platinum(II) 5,10,15,20-tetrakis(pentafluorophenyl)-21H,23H-porphine and the 1,4-bis(diphenylphosphine)butane, 1,3-bis(diphenylphosphino)propane, 2-(2'-di-tert-butylphosphine)biphenyl, acetonitrile, benzonitrile, ethylenediamine, chloroform, 1,2-bis(phenylsulfinyl)ethane, 1,3-bis(2,6-diisopropylphenyimidazolidene)(3-chloropyridyl), 2'-(dimethylamino)-2-biphenylyl, dinorbornylphosphine, 2-(dimethylaminomethyl)ferrocene, allyl, bis(diphenylphosphino)butane, (N-succinimidyl)bis-(triphenylphosphine), dimethylphenylphosphine, methyldiphenylphosphine, 1,10-phenanthroline, 1,5-cyclooctadiene, N,N,N',N'-tetramethylethylenediamine, triphenylphosphine, tri-o-tolylphosphine, tricyclohexylphosphine, tributylphosphine, triethylphosphine, 2,2'-bis(diphenylphosphino)-1,1'-binaphthyl, 1,3-bis(2,6-diisopropylphenyl)-imidazol-2-ylidene, 1,3-bis(mesityl)imidazol-2-ylidene, 1,1'-bis(diphenylphosphino)-ferrocene, 1,2-bis(diphenylphosphino)ethane, N-methylimidazole, 2,2'-bipyridine, (bicyclo[2.2.1]hepta-2,5-diene), bis(di-tert-butyl(4-dimethylaminophenyl)-phosphine), bis(tert-butyl isocyanide), 2-methoxyethyl ether, ethylene glycol dimethyl ether, 1,2-dimethoxyethane, bis(1,3-diamino-2-propanol), bis(N,N-diethylethylenediamine), 1,2-diaminocyclohexane, pyridine, 2,2':6',2"-terpyridine, diethyl sulfide, ethylene and amine complexes thereof; rhodium chloride, rhodium bromide, rhodium iodide, rhodium fluoride, rhodium hydride, rhodium oxide, rhodium peroxide, rhodium cyanide, rhodium sulfate, rhodium nitrate, rhodium phosphide, rhodium boride, rhodium chromium oxide, rhodium cobalt oxide, rhodium carbonate hydroxide, rhodium cyclohexane butyrate, rhodium hydroxide, rhodium molybdate, rhodium octanoate, rhodium oxalate, rhodium perchlorate, rhodium phthalocyanine, rhodium 5,9,14,18,23,27,32,36-octabutoxy-2,3-naphthalocyanine, rhodium sulfamate, rhodium perchlorate, rhodium thiocyanate, rhodium bis(2,2,6,6-tetramethyl-3,5-heptanedionate), rhodium propionate, rhodium acetate, rhodium stearate, rhodium 2-ethylhexanoate, rhodium acetylacetonate, rhodium hexafluoroacetylacetonate, rhodium tetrafluoroborate, rhodium thiosulfate, rhodium trifluoroacetate, rhodium phthalocyaninetetrasulfonic acid tetrasodium salt, rhodium methyl, rhodium cyclopentadienyl, rhodium methylcyclopentadienyl, rhodium ethylcyclopentadienyl, rhodium pentamethylcyclopentadienyl, rhodium 2,3,7,8,12,13,17,18-octaethyl-21H,23H-porphine, rhodium 5,10,15,20-tetraphenyl-21H,23H-porphine, rhodium bis(5-[[4-(dimethylamino)phenyl]imino]-8(5H)-quinolinone), rhodium 2,11,20,29-tetra-tert-butyl-2,3-naphthalocyanine, rhodium 2,9,16,23- tetraphenoxy-29H,31H-phthalocyanine, rhodium 5,10,15, 20-tetrakis(pentafluorophenyl)-21H,23H-porphine and the 1,4-bis(diphenylphosphine)butane, 1,3-bis(diphenylphosphino)propane, 2-(2'-di-tert-butylphosphine)biphenyl, acetonitrile, benzonitrile, ethylenediamine, chloroform, 1,2-bis (phenylsulfinyl)ethane, 1,3-bis(2,6-diisopropylphenyl)-imidazolidene)(3-chloropyridyl), 2'-(dimethylamino)-2-biphenylyl, dinorbornyl-phosphine, 2-(dimethylaminomethyl)ferrocene, allyl, bis(diphenylphosphino)-butane, (N-succinimidyl)bis(triphenylphosphine), dimethylphenylphosphine, methyldiphenylphosphine, 1,10 phenanthroline, 1,5-cyclooctadiene, N,N,N',N'-tetramethylethylenediamine, triphenylphosphine, tri-o-tolylphosphine, tricyclohexylphosphine, tributylphosphine, triethylphosphine, 2,2'-bis(diphenylphosphino)-1,1'-binaphthyl, 1,3-bis (2,6-diisopropylphenyl)-imidazol-2-ylidene, 1,3-bis(mesityl)imidazol-2-ylidene, 1,1'-bis(diphenylphosphino)-ferrocene, 1,2-bis(diphenylphosphino)ethane, N-methylimidazole, 2,2'-bipyridine, (bicyclo[2.2.1]hepta-2, 5-diene), bis(di-tert-butyl(4-dimethylaminophenyl)-phosphine), bis(tert-butyl isocyanide), 2-methoxyethyl ether, ethylene glycol dimethyl ether, 1,2-dimethoxyethane, bis(1,3-diamino-2-propanol), bis(N,N-diethylethylenediamine), 1,2-diaminocyclohexane, pyridine, 2,2':6',2"-terpyridine, diethyl sulfide, ethylene and amine complexes thereof; potassium hexachloropalladate(IV), sodium hexachloropalladate(IV), ammonium hexachloropalladate(IV), potassium tetrachloropalladate(II), sodium tetrachloropalladate(II), ammonium tetrachloropalladate(II), bromo(tri-tert-butylphosphine)palladium(I) dimer, (2-methylallyl)palladium(II) chloride dimer, bis(dibenzylideneacetone)palladium(0), tris(dibenzylideneacetone)dipalladium(0), tetrakis(triphenylphosphine)palladium(0), tetrakis(tricyclohexylphosphine)-palladium(0), bis[1,2-bis(diphenylphosphine)ethane]palladium (0), bis(3,5,3',5'-dimethoxydibenzylideneacetone)palladium (0), bis(tri-tert-butylphosphine)-palladium(0), meso-tetraphenyltetrabenzoporphinepalladium, tetrakis-(methyldiphenylphosphine)palladium(0), tris(3,3',3"-phophinidyne-tris(benzenesulfonato)palladium(0) nonasodium salt, 1,3-bis(2,4,6-trimethyl-phenyl)imidazol-2-ylidene(1,4-naphthoquinone)palladium(0), 1,3-bis(2,6-diisopropylphenyl)imidazol-2-ylidene(1,4-naphthoquinone) palladium(0) and the chloroform complex thereof; allylnickel (II) chloride dimer, ammonionickel(II) sulfate, bis(1,5-cyclooctadiene)nickel(0), bis(triphenylphosphine) dicarbonylnickel(0), tetrakis(triphenyl-phosphine)nickel(0), tetrakis(triphenylphosphite)nickel(0), potassium hexafluoronickelate(IV), potassium tetracyanonickelate(II), potassium nickel(IV) paraperiodate, dilithium tetrabromonickelate(II), potassium tetracyanonickelate(II); platinum(IV) chloride, platinum(IV) oxide, platinum(IV) sulfide, potassium hexachloroplatinate(IV), sodium hexachloroplatinate (IV), ammonium hexachloroplatinate(IV), potassium tetrachloroplatinate(II), ammonium tetrachloroplatinate(II), potassium tetracyanoplatinate(II), trimethyl(methylcyclopentadienyl)platinum(IV), cis-diamminetetrachloroplatinum (IV), potassium trichloro(ethylene)platinate(II), sodium hexahydroxyplatinate(IV), tetraamineplatinum(II)tetrachloroplatinate(II), tetrabutylammonium hexachloroplatinate (IV), ethylenebis(triphenylphosphine)platinum(0), platinum (0) 1,3-divinyl-1,1,3,3-tetramethyldisiloxane, platinum(0) 2,4,6,8-tetramethyl-2,4,6,8-tetravinylcyclotetrasiloxane, tetrakis(triphenylphosphine)platinum(0), platinum octaethylporphyrin, chloroplatinic acid, carboplatin; chlorobis(ethylene)rhodium dimer, hexarhodium hexadecacarbonyl, chloro-(1,5-cyclooctadiene)rhodium dimer chloro(norbornadiene)rhodium dimer, chloro(1,5-hexadiene)rhodium dimer.

The ligands preferably comprise phosphines of the formula (VI)

$PR^8_3$ (VI)

in which the $R^8$ radicals are each independently hydrogen, straight-chain, branched or cyclic $C_1$-$C_{20}$-alkyl, $C_6$-$C_{20}$-alkylaryl, $C_2$-$C_{20}$-alkenyl, $C_2$-$C_{20}$-alkynyl, $C_1$-$C_{20}$-carboxylate, $C_1$-$C_{20}$-alkoxy, $C_2$-$C_{20}$-alkenyloxy, $C_2$-$C_{20}$-alkynyloxy, $C_2$-$C_{20}$-alkoxycarbonyl, $C_1$-$C_{20}$-alkylthio, $C_1$-$C_{20}$-alkylsulfonyl, $C_1$-$C_{20}$-alkylsulfinyl, silyl and/or derivatives thereof and/or phenyl substituted by at least one $R^9$, or naphthyl substituted by at least one $R^9$. Each $R^9$ is independently hydrogen, fluorine, chlorine, bromine, iodine, $NH_2$, nitro, hydroxyl, cyano, formyl, straight-chain, branched or cyclic $C_1$-$C_{20}$-alkyl, $C_1$-$C_{20}$-alkoxy, $HN(C_1$-$C_{20}$-alkyl), $N(C_1$-$C_{20}$-alkyl)$_2$, —$CO_2$—($C_1$-$C_{20}$-alkyl), —$CON(C_1$-$C_{20}$-alkyl)$_2$, —$OCO(C_1$-$C_{20}$-alkyl), $NHCO(C_1$-$C_{20}$-alkyl, $C_1$-$C_{20}$-acyl, —$SO_3M$, —$SO_2N(R^{10})M$, —$CO_2M$, —$PO_3M_2$, —$AsO_3M_2$, —$SiO_2M$, —$C(CF_3)_2OM(M=H, Li, Na or K)$, where $R^{10}$ is hydrogen, fluorine, chlorine, bromine, iodine, straight-chain, branched or cyclic $C_1$-$C_{20}$-alkyl, $C_2$-$C_{20}$-alkenyl, $C_2$-$C_{20}$-alkynyl, $C_1$-$C_{20}$-carboxylate, $C_1$-$C_{20}$-alkoxy, $C_2$-$C_{20}$-alkenyloxy, $C_2$-$C_{20}$-alkynyloxy, $C_2$-$C_{20}$-alkoxycarbonyl, $C_1$-$C_{20}$-alkylthio, $C_1$-$C_{20}$-alkylsulfonyl, $C_1$-$C_{20}$-alkylsulfinyl, silyl and/or their derivatives, aryl, $C_6$-$C_{20}$-arylalkyl, $C_6$-$C_{20}$-alkylaryl, phenyl and/or biphenyl. Preferably, the $R^8$ groups are all identical.

Suitable phosphines (VI) are for example trimethylphosphine, triethylphosphine, tripropylphosphine, triisopropylphosphine, tributylphosphine, triisobutylphosphine, triisopentylphosphine, trihexylphosphine, tricyclohexylphosphine, trioctylphosphine, tridecylphosphine, triphenylphosphine, diphenylmethylphosphine, phenyldimethylphosphine, tri(o-tolyl)phosphine, tri(p-tolyl) phosphine, ethyldiphenylphosphine, dicyclohexylphenylphosphine, 2-pyridyldiphenylphosphine, bis(6-methyl-2-pyridyl)phenylphosphine, tri(p-chlorophenyl)phosphine, tri(p-methoxyphenyl)phosphine, diphenyl(2-sulfonatophenyl)phosphine; potassium, sodium and ammonium salts of diphenyl(3-sulfonatophenyl)phosphine, bis(4, 6-dimethyl-3-sulfonatophenyl)(2,4-dimethylphenyl) phosphine, bis(3-sulfonatophenyl)phenylphosphines, tris(4, 6-dimethyl-3-sulfonatophenyl)-phosphines, tris(2-sulfonatophenyl)phosphines, tris(3-sulfonatophenyl) phosphines; 2-bis(diphenylphosphinoethyl) trimethylammonium iodide, 2'-dicyclohexylphosphino-2,6-dimethoxy-3-sulfonato-1,1'-biphenyl sodium salt, trimethyl phosphite and/or triphenyl phosphite.

The ligands more preferably comprise bidentate ligands of the general formula

$R^8M''$-$Z$-$M''R^8$ (VII).

In this formula, each M" is independently N, P, As or Sb. The two M" are preferably the same, and M" is more preferably a phosphorus atom.

Each $R^8$ group independently represents the radicals described under formula (VI). The $R^8$ groups are preferably all identical.

Z is preferably a bivalent bridging group which contains at least 1 bridging atom, preferably from 2 to 6 bridging atoms.

Bridging atoms can be selected from carbon, nitrogen, oxygen, silicon and sulfur atoms. Z is preferably an organic bridging group containing at least one carbon atom. Z is preferably an organic bridging group containing 1 to 6 bridging atoms, of which at least two are carbon atoms, which may be substituted or unsubstituted.

Preferred Z groups are —CH$_2$—, —CH$_2$—CH$_2$—, —CH$_2$—CH$_2$—CH$_2$—, —CH$_2$—CH(CH$_3$)—CH$_2$—, —CH$_2$—C(CH$_3$)$_2$—CH$_2$—, —CH$_2$—C(C$_2$H$_5$)—CH$_2$—, —CH$_2$—Si(CH$_3$)$_2$—CH$_2$—, —CH$_2$—O—CH$_2$—, —CH$_2$—CH$_2$—CH$_2$—CH$_2$—, —CH$_2$—CH(C$_2$H$_5$)—CH$_2$—, —CH$_2$—CH(n-Pr)—CH and —CH$_2$—CH(n-Bu)—CH$_2$—, substituted or unsubstituted 1,2-phenyl, 1,2-cyclohexyl, 1,1'- or 1,2-ferrocenyl radicals, 2,2"-(1,1"-biphenyl), 4,5-xanthene and/or oxydi-2,1-phenylene radicals.

Examples of suitable bidentate phosphine ligands (VII) are 1,2-bis-(dimethylphosphino)ethane, 1,2-bis(diethylphosphino)ethane, 1,2-bis-(dipropylphosphino)ethane, 1,2-bis(diisopropylphosphino)ethane, 1,2-bis(dibutylphosphino)ethane, 1,2-bis(di-tert-butylphosphino)ethane, 1,2-bis-(dicyclohexylphosphino)ethane, 1,2-bis(diphenylphosphino)ethane; 1,3-bis(dicyclohexylphosphino)propane, 1,3-bis(diisopropylphosphino)propane, 1,3-bis(di-tert-butylphosphino)propane, 1,3-bis(diphenylphosphino)propane; 1,4-bis(diisopropylphosphino)butane, 1,4-bis(diphenylphosphino)butane; 1,5-bis(dicyclohexylphosphino)pentane; 1,2-bis(di-tert-butylphosphino)benzene, 1,2-bis(diphenylphosphino)benzene, 1,2-bis(dicyclohexylphosphino)benzene, 1,2-bis(dicyclopentylphosphino)benzene, 1,3-bis(di-tert-butylphosphino)benzene, 1,3-bis(diphenylphosphino)benzene, 1,3-bis(dicyclohexylphosphino)benzene, 1,3-bis(dicyclopentylphosphino)benzene; 9,9-dimethyl-4,5-bis(diphenylphosphino)-xanthene, 9,9-dimethyl-4,5-bis(diphenylphosphino)-2,7-di-tert-butylxanthene, 9,9-dimethyl-4,5-bis(di-tert-butylphosphino)xanthene, 1,1'-bis(diphenylphosphino)-ferrocene, 2,2'-bis(diphenylphosphino)-1,1'-binaphthyl, 2,2'-bis(di-p-tolylphosphino)-1,1'-binaphthyl, (oxydi-2,1-phenylene)bis(diphenylphosphine), 2,5-(diisopropylphospholano)benzene, 2,3-O-isopropylidene-2,3-dihydroxy-1,4-bis(diphenylphosphino)butane, 2,2'-bis(di-tert-butylphosphino)-1,1'-biphenyl, 2,2'-bis(dicyclohexylphosphino)-1,1'-biphenyl, 2,2'-bis(diphenylphosphino)-1,1'-biphenyl, 2-(di-tert-butylphosphino)-2'-(N,N-dimethylamino)biphenyl, 2-(dicyclohexylphosphino)-2'-(N,N-dimethylamino)biphenyl, 2-(diphenylphosphino)-2'-(N,N-dimethylamino)biphenyl, 2-(diphenylphosphino)ethylamine, 2-[2-(diphenylphosphino)ethyl]pyridine; potassium, sodium and ammonium salts of 1,2-bis(di-4-sulfonatophenylphosphino)benzene, (2,2'-bis[[bis(3-sulfonatophenyl)phosphino]methyl]-4,4',7,7'-tetrasulfonato-1,1'-binaphthyl, (2,2'-bis[[bis(3-sulfonatophenyl)phosphino]methyl]-5,5'-tetrasulfonato-1,1'-biphenyl, (2,2'-bis[[bis(3-sulfonatophenyl)phosphino]methyl]-1,1-binaphthyl, (2,2'-bis[[bis(3-sulfonatophenyl)phosphino]methyl]-1,1'-biphenyl, 9,9-dimethyl-4,5-bis(diphenylphosphino)-2,7-sulfonatoxanthene, 9,9-dimethyl-4,5-bis(di-tert-butylphosphino)-2,7-sulfonatoxanthene, 1,2-bis(di-4-sulfonatophenylphosphino)-benzene, meso-tetrakis(4-sulfonatophenyl)porphine, meso-tetrakis(2,6-dichloro-3-sulfonatophenyl)porphine, meso-tetrakis(3-sulfonatomesityl)porphine, tetrakis(4-carboxyphenyl)porphine and 5,11,17,23-sulfonato-25,26,27,28-tetrahydroxycalix[4]arene.

Moreover, the ligands of the formula (VI) and (VII) can be attached to a suitable polymer or inorganic substrate by the R$^8$ radicals and/or the bridging group.

The molar transition metal/ligand ratio of the catalyst system is in the range from 1:0.01 to 1:100, preferably in the range from 1:0.05 to 1:10 and more preferably in the range from 1:1 to 1:4.

The reactions in the process stages a), b) and c) preferably take place, if desired, in an atmosphere comprising further gaseous constituents such as nitrogen, oxygen, argon, carbon dioxide for example; the temperature is in the range from −20 to 340° C., more particularly in the range from 20 to 180° C., and total pressure is in the range from 1 to 100 bar.

The products and/or the transition metal and/or the transition metal compound and/or catalyst system and/or the ligand and/or starting materials are optionally isolated after the process stages a), b) and c) by distillation or rectification, by crystallization or precipitation, by filtration or centrifugation, by adsorption or chromatography or other known methods.

According to the present invention, solvents, auxiliaries and any other volatile constituents are removed by distillation, filtration and/or extraction for example.

The reactions in the process stages a), b) and c) are preferably carried out, if desired, in absorption columns, spray towers, bubble columns, stirred tanks, trickle bed reactors, flow tubes, loop reactors and/or kneaders.

Suitable mixing elements include for example anchor, blade, MIG, propeller, impeller and turbine stirrers, cross beaters, disperser disks, hollow (sparging) stirrers, rotor-stator mixers, static mixers, Venturi nozzles and/or mammoth pumps.

The intensity of mixing experienced by the reaction solutions/mixtures preferably corresponds to a rotation Reynolds number in the range from 1 to 1 000 000 and preferably in the range from 100 to 100 000.

Preferably, the respective reactants etc. are mixed intensively with an energy input in the range from 0.080 to 10 kW/m$^3$, preferably 0.30-1.65 kW/m$^3$.

During the reaction, the catalyst A is preferably homogeneous and/or heterogeneous in action.

Preferably, the catalyst A is generated in situ before the reaction and/or at the start of the reaction and/or during the reaction.

Preferably, the particular heterogeneous catalyst acts during the reaction as a suspension or bound to a solid phase.

The reactions of the present invention can be carried out in liquid phase, in the gas phase or else in supercritical phase. The catalyst A is preferably used in the case of liquids in homogeneous form or as a suspension, while a fixed bed arrangement is advantageous in the case of gas phase or supercritical operation.

Suitable solvents are water, alcohols, e.g. methanol, ethanol, isopropanol, n-propanol, n-butanol, isobutanol, tert-butanol, n-amyl alcohol, isoamyl alcohol, tert-amyl alcohol, n-hexanol, n-octanol, isooctanol, n-tridecanol, benzyl alcohol, etc. Preference is further given to glycols, e.g. ethylene glycol, 1,2-propanediol, 1,3-propanediol, 1,3-butanediol, 1,4-butanediol, diethylene glycol etc.; aliphatic hydrocarbons, such as pentane, hexane, heptane, octane, and petroleum ether, naphtha, kerosene, petroleum, paraffin oil, etc.; aromatic hydrocarbons, such as benzene, toluene, xylene, mesitylene, ethylbenzene, diethylbenzene, etc.; halogenated hydrocarbons, such as methylene chloride, chloroform, 1,2-dichloroethane, chlorobenzene, carbon tetrachloride, tetrabromoethylene, etc.; alicyclic hydrocarbons, such as cyclopentane, cyclohexane, and methylcyclohexane, etc.; ethers, such as anisole (methyl phenyl ether), tert-butyl methyl ether, dibenzyl ether, diethyl ether, dioxane, diphenyl ether, methyl vinyl ether, tetrahydrofuran, triisopropyl ether etc.; glycol ethers, such as diethylene glycol diethyl ether, diethylene glycol dimethyl ether (diglyme), diethylene glycol monobutyl ether, diethylene glycol monomethyl ether, 1,2-dimethoxyethane (DME, monoglyme), ethylene glycol monobutyl ether, triethylene glycol dimethyl ether (triglyme), triethylene glycol monomethyl ether etc.; ketones, such as acetone, diisobutyl ketone, methyl n-propyl ketone; methyl ethyl ketone, methyl isobutyl ketone etc.; esters, such as methyl formate, methyl acetate, ethyl acetate, n-propyl acetate, and n-butyl acetate, etc.; carboxylic acids, such as formic acid, acetic acid, propionic acid, butyric acid, etc., each alone or in combination with one another.

Suitable solvents also encompass the phosphinic acid sources and olefins used. These have advantages in the form of higher space-time yield.

Preferably, the reaction is carried out under the autogenous vapor pressure of the olefin and/or of the solvent.

Preferably, $R^1$, $R^2$, $R^3$ and $R^4$ of olefin (IV) are the same or different and are each independently H, methyl, ethyl, n-propyl, isopropyl, n-butyl, isobutyl, tert-butyl and/or phenyl.

Preference is also given to using functionalized olefins such as allyl isothiocyanate, allyl methacrylate, 2-allylphenol, N-allylthiourea, 2-(allylthio)-2-thiazoline, allyltrimethylsilane, allyl acetate, allyl acetoacetate, allyl alcohol, allylamine, allylbenzene, allyl cyanide, allyl cyanoacetate, allylanisole, trans-2-pentenal, cis-2-pentenenitrile, 1-penten-3-ol, 4-penten-1-ol, 4-penten-2-ol, trans-2-hexenal, trans-2-hexen-1-ol, cis-3-hexen-1-ol, 5-hexen-1-ol, styrene, -methylstyrene, 4-methylstyrene, vinyl acetate, 9-vinylanthracene, 2-vinylpyridine, 4-vinylpyridine and/or 1-vinyl-2-pyrrolidone.

Preferably, the reaction is effected at a partial pressure of the olefin of 0.01-100 bar, more preferably at a partial pressure of the olefin of 0.1-10 bar.

Preferably, the reaction is effected in a molar phosphinic acid/olefin ratio of from 1:10 000 to 1:0.001, more preferably of 1:30 to 1:0.01.

Preferably, the reaction is effected in a molar phosphinic acid/catalyst ratio of from 1:1 to 1:0.00000001, more preferably at 1:0.01 to 1:0.000001.

Preferably, the reaction is effected in a molar phosphinic acid/solvent ratio of from 1:10 000 to 1:0, more preferably at 1:50 to 1:1.

One process according to the invention for preparing compounds of the formula (II) comprises reacting a phosphinic acid source with olefins in the presence of a catalyst and freeing the product (II) (alkylphosphonous acid, salts or esters) of catalyst, transition metal or transition metal compound, ligand, complexing agent, salts and by-products.

The present invention provides that the catalyst, the catalyst system, the transition metal and/or the transition metal compound are separated off by adding an auxiliary 1 and removing the catalyst, the catalyst system, the transition metal and/or the transition metal compound by extraction and/or filtration.

The present invention provides that the ligand and/or complexing agent is separated off by extraction with auxiliary 2 and/or distillation with auxiliary 2.

Auxiliary 1 is preferably water and/or at least one member of the group of metal scavengers. Preferred metal scavengers are metal oxides, such as aluminum oxide, silicon dioxide, titanium dioxide, zirconium dioxide, zinc oxide, nickel oxide, vanadium oxide, chromium oxide, magnesium oxide, Celite®, kieselguhr; metal carbonates, such as barium carbonate, calcium carbonate, strontium carbonate; metal sulfates, such as barium sulfate, calcium sulfate, strontium sulfate; metal phosphates, such as aluminum phosphate, vanadium phosphate, metal carbides, such as silicone carbide; metal aluminates, such as calcium aluminate; metal silicates, such as aluminum silicate, chalks, zeolites, bentonite, montmorillonite, hectorite; functionalized silicates, functionalized silica gels, such as SiliaBond®, QuadraSil™; functionalized polysiloxanes, such as Deloxan®; metal nitrides, carbon, activated carbon, mullite, bauxite, antimonite, scheelite, perovskite, hydrotalcite, functionalized and unfunctionalized cellulose, chitosan, keratin, heteropolyanions, ion exchangers, such as Amberlite™, Amberjet™, Ambersep™, Dowex®, Lewatit®, ScavNet®; functionalized polymers, such as Chelex®, QuadraPure™, Smopex®, PolyOrgs®; polymer-bound phosphanes, phosphane oxides, phosphinates, phosphonates, phosphates, amines, ammonium salts, amides, thioamides, ureas, thioureas, triazines, imidazoles, pyrazoles, pyridines, pyrimidines, pyrazines, thiols, thiol ethers, thiol esters, alcohols, alkoxides, ethers, esters, carboxylic acids, acetates, acetals, peptides, hetarenes, polyethyleneimine/silicon dioxide, and/or dendrimers.

Preferably, auxiliary 1 is added in amounts corresponding to 0.1-40% by weight loading of the metal on auxiliary 1.

Preferably, auxiliary 1 is used at temperatures of 20-90° C.

Preferably, the residence time of auxiliary 1 is 0.5-360 minutes.

Auxiliary 2 is preferably the aforementioned solvent of the present invention, as preferably used in process stage a).

The esterification of the ethylenedialkylphosphinic acid (III) or of the alkyl-phosphonous acid derivatives (II), and of the phosphinic acid source (I) to form the corresponding esters can be achieved, for example, by reaction with higher-boiling alcohols by removing the resultant water by azeotropic distillation, or by reaction with epoxides (alkylene oxides).

Preferably, following step a), the alkylphosphonous acid (II) is directly esterified with an alcohol of the general formula M-OH and/or M'-OH or by reaction with alkylene oxides, as indicated below.

M-OH preferably comprises primary, secondary or tertiary alcohols having a carbon chain length of $C_1$-$C_{18}$. Particular preference is given to methanol, ethanol, propanol, isopropanol, n-butanol, 2-butanol, tert-butanol, amyl alcohol and/or hexanol.

M'-OH preferably comprises ethylene glycol, 1,2-propylene glycol, 1,3-propylene glycol, 1,4-butanediol, 2,2-dimethylpropane-1,3-diol, neopentyl glycol, 1,6-hexanediol, 1,4-cyclohexanedimethanol, glycerol, trishydroxymethylethane, trishydroxymethylpropane, pentaerythritol, sorbitol, mannitol, α-naphthol, polyethylene glycols, polypropylene glycols and/or EO-PO block polymers.

Also suitable as M-OH and M'-OH are mono- or polyhydric unsaturated alcohols having a carbon chain length of $C_1$-$C_{18}$, for example n-but-2-en-1-ol, 1,4-butenediol and allyl alcohol.

Also suitable as M-OH and M'-OH are reaction products of monohydric alcohols with one or more molecules of alkylene oxides, preferably with ethylene oxide and/or 1,2-propylene oxide. Preference is given to 2-methoxyethanol, 2-ethoxyethanol, 2-n-butoxyethanol, 2-(2'-ethylhexyloxy)ethanol, 2-n-dodecoxy-ethanol, methyl diglycol, ethyl diglycol, isopropyl diglycol, fatty alcohol polyglycol ethers and aryl polyglycol ethers.

M-OH and M'-OH are also preferably reaction products of polyhydric alcohols with one or more molecules of alkylene oxide, more particularly diglycol and triglycol and also adducts of 1 to 6 molecules of ethylene oxide or propylene oxide onto glycerol, trishydroxymethylpropane or pentaerythritol.

The M-OH and M'-OH used may also be reaction products of water with one or more molecules of alkylene oxide. Preference is given to polyethylene glycols and poly-1,2-propylene glycols of various molecular sizes having an average molecular weight of 100-1000 g/mol and more preferably of 150-350 g/mol.

Preference for use as M-OH and M'-OH is also given to reaction products of ethylene oxide with poly-1,2-propylene glycols or fatty alcohol propylene glycols; similarly reaction products of 1,2-propylene oxide with polyethylene glycols or fatty alcohol ethoxylates. Preference is given to such reaction products with an average molecular weight of 100-1000 g/mol, more preferably of 150-450 g/mol.

Also usable as M-OH and M'-OH are reaction products of alkylene oxides with ammonia, primary or secondary amines, hydrogen sulfide, mercaptans, oxygen acids of phosphorus and $C_2$-$C_6$ dicarboxylic acids. Suitable reaction products of ethylene oxide with nitrogen compounds are triethanolamine, methyldiethanolamine, n-butyldiethanolamine, n-dodecyldiethanolamine, dimethylethanolamine, n-butylmethylethanolamine, di-n-butylethanolamine, n-dodecylmethylethanolamine, tetrahydroxyethylethylenediamine or pentahydroxyethyldiethylenetriamine.

Preferred alkylene oxides are ethylene oxide, 1,2-propylene oxide, 1,2-epoxybutane, 1,2-epoxyethylbenzene, (2,3-epoxypropyl)benzene, 2,3-epoxy-1-propanol and 3,4-epoxy-1-butene.

Suitable solvents are the solvents mentioned in process step a) and also the M-OH and M'-OH alcohols used and the alkylene oxides. These offer advantages in the form of a higher space-time yield.

The reaction is preferably carried out under the autogenous vapor pressure of the employed alcohol M-OH, M'-OH and alkylene oxide and/or of the solvent.

Preferably, the reaction is carried out at a partial pressure of the employed alcohol M-OH, M'-OH and alkylene oxide of 0.01-100 bar, more preferably at a partial pressure of the alcohol of 0.1-10 bar.

Preferably, the reaction is carried out at a temperature of from −20 to 340° C., more preferably at a temperature of from 20 to 180° C.

Preferably, the reaction is carried out at a total pressure of from 1 to 100 bar.

Preferably, the reaction is carried out in a molar ratio of the alcohol or alkylene oxide component to the phosphinic acid source (I) or alkylphosphonous acid (II) or ethylenedialkyiphosphinic acid (III) of from 10000:1 to 0.001:1, more preferably in a ratio of 1000:1 to 0.01:1.

Preferably, the reaction is carried out in a molar ratio of the phosphinic acid source (I) or alkylphosphonous acid (II) or ethylenedialkylphosphinic acid (III) to the solvent of from 1:10 000 to 1:0, more preferably in a molar phosphinic acid/solvent ratio of from 1:50 to 1:1.

Particularly preferred catalysts B, as used in process stage b), are peroxo compounds such as peroxomonosulfuric acid, potassium monopersulfate (potassium peroxomonosulfate), Caroat™, Oxone™, peroxodisulfuric acid, potassium persulfate (potassium peroxodisulfate), sodium persulfate (sodium peroxodisulfate), ammonium persulfate (ammonium peroxodisulfate).

Preferred catalysts B are additionally compounds capable of forming peroxides in the solvent system, such as sodium peroxide, sodium peroxide diperoxohydrate, sodium peroxide diperoxohydratehydrate, sodium peroxide dihydrate, sodium peroxide octahydrate, lithium peroxide, lithium peroxide monoperoxohydratetrihydrate, calcium peroxide, strontium peroxide, barium peroxide, magnesium peroxide, zinc peroxide, potassium hyperoxide, potassium peroxide diperoxohydrate, sodium peroxoborate tetrahydrate, sodium peroxoborate trihydrate, sodium peroxoborate monohydrate, anhydrous sodium peroxoborate, potassium peroxoborate peroxohydrate, magnesium peroxoborate, calcium peroxoborate, barium peroxoborate, strontium peroxoborate, potassium peroxoborate, peroxomonophosphoric acid, peroxodiphosphoric acid, potassium peroxodiphosphate, ammonium peroxodiphosphate, potassium ammonium peroxodiphosphates (double salt), sodium carbonate peroxohydrate, urea peroxohydrate, ammonium oxalate peroxide, barium peroxide peroxohydrate, barium peroxide peroxohydrate, calcium hydrogen peroxides, calcium peroxide peroxohydrate, ammonium triphosphate diperoxophosphate hydrate, potassium fluoride peroxohydrate, potassium fluoride triperoxohydrate, potassium fluoride diperoxohydrate, sodium pyrophosphate diperoxohydrate, sodium pyrophosphate diperoxohydrate octahydrate, potassium acetate peroxohydrate, sodium phosphate peroxohydrate, sodium silicate peroxohydrate.

Preferred catalysts B are also hydrogen peroxide, performic acid, peracetic acid, benzoyl peroxide, di-tert-butyl peroxide, dicumyl peroxide, 2,4-dichlorobenzoyl peroxide, decanoyl peroxide, lauryl peroxide, cumene hydroperoxide, pinene hydroperoxide, p-menthane hydroperoxide, tert-butyl hydroperoxide, acetylacetone peroxide, methyl ethyl ketone peroxide, succinic acid peroxide, dicetyl peroxydicarbonate, tert-butyl peroxyacetate, tert-butylperoxymaleic acid, tert-butyl peroxybenzoate, acetyl cyclohexylsulfonyl peroxide.

Preferred catalysts B are also water-soluble azo compounds. Particular preference is given to azo initiators such as VAZO® 52 2,2'-azobis(2,4-dimethylvaleronitrile), VAZO® 64 (azobis(isobutyronitrile), AIBN), VAZO® 67 2,2'-azobis(2-methyl-butyronitrile), VAZO® 88 1,1'-azobis(cyclohexane-1-carbonitrile), VAZO® 68 from Dupont-Biesteritz, V-70 2,2'-azobis(4-methoxy-2,4-dimethylvaleronitrile), V-65 2,2'-azobis(2,4-dimethylvaleronitrile), V-601 dimethyl 2,2'-azobis(2-methylpropionate), V-59 2,2'-azobis(2-methylbutyronitrile), V-40 1,1'-azobis(cyclohexane-1-carbonitrile), VF-096 2,2'-azobis[N-(2-propenyl)-2-methylpropionamide], V-30 1-[(cyano-1-methylethyl)azo]formamide, VAm-110 2,2'-azobis(N-butyl-2-methyl-propionamide), VAm-111 2,2'-azobis(N-cyclohexyl-2-methylpropionamide), VA-046B 2,2'-azobis[2-(2-imidazolin-2-yl)propane disulfate dihydrate, VA-057 2,2'-azobis[N-(2-carboxyethyl)-2-methylpropionamidine]tetrahydrate, VA-061 2,2'-azobis[2-(2-imidazolin-2-yl)propane], VA-080 2,2'-azobis{2-methyl-N-[1,1-bis-(hydroxymethyl)-2-hydroxyethyl]propionamide, VA-085 2,2'-azobis{2-methyl-N-[2-(1-hydroxybutyl)]propionamide}, VA-086 2,2'-azobis[2-methyl-N-(2-hydroxyethyl)propionamide] from Wako Chemicals.

Also suitable are azo initiators such as 2-tert-butylazo-2-cyanopropane, dimethyl azodiisobutyrate, azodiisobutyronitrile, 2-tert-butylazo-1-cyanocyclohexane, 1-tert-amylazo-1-cyanocyclohexane. Preference is further given to alkyl perketals such as 2,2-bis(tert-butylperoxy)butane, ethyl 3,3-bis(tert-butylperoxy)butyrate, 1,1-di(tert-butylperoxy)cyclohexane.

Preferably, the catalyst B is used in amounts of 0.05 to 5 mol %, based on the particular acetylenic compound (V).

Preferably, the catalyst B is used in amounts of 0.001 to 10 mol %, based on the phosphorus compound.

Preferably, the catalyst B is metered in continuously during the reaction.

Preferably, the catalyst B is metered in continuously during the reaction in the form of a solution in the acetylenic compound (V).

Preferably, the catalyst B is metered in continuously during the reaction in the form of a solution in the solvent used.

Preferably, the acetylenic compounds (V) are acetylene, methylacetylene, 1-butyne, 1-hexyne, 2-hexyne, 1-octyne, 4-octyne, 1-butyn-4-ol, 2-butyn-1-ol, 3-butyn-1-ol, 5-hexyn-1-ol, 1-octyn-3-ol, 1-pentyne, phenylacetylene and/or trimethylsilylacetylene.

Suitable solvents are those mentioned for step a).

Preferably, the alkylphosphonous acids (II) are reacted with the acetylenic compound (V) at a temperature of 0 to 250° C., more preferably at a temperature of 20 to 200° C. and especially at a temperature of 50 to 150° C.

Preferably, the atmosphere in the reaction with the acetylenic compound (V) consists to an extent of 50 to 99.9% by weight of constituents of the solvents and of the acetylenic compound (V), preferably 70-95%.

Preferably, the reaction during the addition of the acetylenic compound (V) is effected at a pressure of 1-20 bar.

The subject matter of the present invention especially also comprises a process in which an alkylphosphonous acid (II) is reacted with an acetylenic compound (V) in the presence of a catalyst B, and the former is removed continuously from the reaction mixture by circulation filtration and the spent alkylphosphonous acid (II) is likewise continuously replaced by new material.

In a further embodiment of the process, the product mixture obtained after process stage a) and/or b) is worked up.

In a further embodiment of the process, the product mixture obtained after process stage a) is worked up, and then the ethylenedialkylphosphinic acids and/or esters and alkali metal salts thereof which are obtained after process stage b) are converted in process stage c).

The ethylenedialkylphosphinic acid (III), or salt thereof, can subsequently be converted to further metal salts.

Preferably, the metal compounds used in process stage c) are compounds of the metals Mg, Ca, Al, Sb, Sn, Ge, Ti, Fe, Zr, Zn, Ce, Bi, Sr, Mn, Li, Na, K, more preferably Mg, Ca, Al, Ti, Zn, Sn, Ce, Fe.

Suitable solvents for process stage c) are those as used above in process stage a).

Preferably, the reaction in process stage c) is effected in an aqueous medium.

Preferably, in process stage c), the ethylenedialkylphosphinic acids (III), and/or esters and/or alkali metal salts thereof, obtained after process stage b) are reacted with metal compounds of Mg, Ca, Al, Zn, Ti, Sn, Zr, Ce or Fe to give the ethylenedialkylphosphinic salts (III) of these metals.

This reaction is effected in a molar ratio of ethylenedialkylphosphinic acid/ester/salt (III) to metal of 8:1 to 1:8 (for tetravalent metal ions or metals with a stable tetravalent oxidation state), of 6:1 to 1:6 (for trivalent metals or metals with a stable trivalent oxidation state), of 4:1 to 1:4 (for divalent metals or metals with a stable divalent oxidation state) and of 3:1 to 1:3 (for monovalent metal ions or metals with a stable monovalent oxidation state).

Preferably, ethylenedialkylphosphinic ester/salt (III) obtained in process stage b) is converted to the corresponding ethylenedialkylphosphinic acid, and the latter is reacted in process stage c) with metal compounds of Mg, Ca, Al, Zn, Ti, Sn, Zr, Ce or Fe to give the ethylenedialkylphosphinic salts (III) of these metals.

Preferably, ethylenedialkylphosphinic acid/ester (III) obtained in process stage b) is converted to an ethylenedialkylphosphinic acid alkali metal salt, and the latter is reacted in process stage c) with metal compounds of Mg, Ca, Al, Zn, Ti, Sn, Zr, Ce or Fe to give the ethylenedialkylphosphinic salts (III) of these metals.

The metal compounds of Mg, Ca, Al, Zn, Ti, Sn, Zr, Ce or Fe for process stage c) preferably comprise metals, metal oxides, hydroxides, oxide hydroxides, borates, carbonates, hydroxocarbonates, hydroxocarbonate hydrates, mixed metal hydroxocarbonates, mixed metal hydroxocarbonate hydrates, phosphates, sulfates, sulfate hydrates, hydroxosulfate hydrates, mixed metal hydroxosulfate hydrates, oxysulfates, acetates, nitrates, fluorides, fluoride hydrates, chlorides, chloride hydrates, oxychlorides, bromides, iodides, iodide hydrates, carboxylic acid derivatives and/or alkoxides.

The metal compounds preferably comprise aluminum chloride, aluminum hydroxide, aluminum nitrate, aluminum sulfate, titanyl sulfate, zinc nitrate, zinc oxide, zinc hydroxide and/or zinc sulfate.

Also suitable are aluminum metal, fluoride, hydroxychloride, bromide, iodide, sulfide, selenide; phosphide, hypophosphite, antimonide, nitride; carbide, hexafluorosilicate; hydride, calcium hydride, borohydride; chlorate; sodium aluminum sulfate, aluminum potassium sulfate, aluminum ammonium sulfate, nitrate, metaphosphate, phosphate, silicate, magnesium silicate, carbonate, hydrotalcite, sodium carbonate, borate; thiocyanate; oxide, oxide hydroxide, their corresponding hydrates and/or polyaluminum hydroxy compounds, which preferably have an aluminum content of 9 to 40% by weight.

Also suitable are aluminum salts of mono-, di-, oligo-, polycarboxylic acids, for example, aluminum diacetate, acetotartrate, formate, lactate, oxalate, tartrate, oleate, palmitate, stearate, trifluoromethanesulfonate, benzoate, salicylate, 8-oxyquinolate.

Likewise suitable are elemental, metallic zinc and also zinc salts, for example zinc halides (zinc fluoride, zinc chlorides, zinc bromide, zinc iodide).

Also suitable are zinc borate, carbonate, hydroxide carbonate, silicate, hexafluorosilicate, stannate, hydroxide stannate, magnesium aluminum hydroxide carbonate; nitrate, nitrite, phosphate, pyrophosphate; sulfate, phosphide, selenide, telluride and zinc salts of the oxoacids of the seventh main group (hypohalites, halites, halates, for example zinc iodate, perhalates, for example zinc perchlorate); zinc salts of the pseudohalides (zinc thiocyanate, zinc cyanate, zinc cyanide); zinc oxides, peroxides, hydroxides or mixed zinc oxide hydroxides.

Preference is given to zinc salts of the oxoacids of transition metals (for example zinc chromate(VI) hydroxide, chromite, permanganate, molybdate).

Also suitable are zinc salts of mono-, di-, oligo-, polycarboxylic acids, for example zinc formate, acetate, trifluoroacetate, propionate, butyrate, valerate, caprylate, oleate, stearate, oxalate, tartrate, citrate, benzoate, salicylate, lactate, acrylate, maleate, succinate, salts of amino acids (glycine), of acidic hydroxyl functions (zinc phenoxide etc), zinc p-phenolsulfonate, acetylacetonate, stannate, dimethyldithiocarbamate, trifluoromethanesulfonate.

In the case of titanium compounds, preference is given to metallic titanium and, as is the case for titanium(III) and/or (IV), to the chloride, nitrate, sulfate, formate, acetate, bromide, fluoride, oxychloride, oxysulfate, oxide, n-propoxide, n-butoxide, isopropoxide, ethoxide, 2-ethylhexyl oxide.

Also suitable is metallic tin and also tin salts (tin(II) and/or (IV) chloride); tin oxides and tin alkoxide such as, for example, tin(IV) tert-butoxide.

Cerium(III) fluoride, chloride and nitrate are also suitable.

In the case of zirconium compounds, metallic zirconium is preferred, as are zirconium salts such as zirconium chloride, zirconium sulfate, zirconyl acetate, zirconyl chloride. Zirconium oxides and also zirconium(IV) tert-butoxide are also preferred.

The reaction in process stage c) is effected at a solids content of the ethylene-dialkylphosphinic salts of from 0.1 to 70% by weight, preferably 5 to 40% by weight.

The reaction in process stage c) is effected at a temperature of 20 to 250° C., preferably at a temperature of 80 to 120° C.

The reaction in process stage c) is effected at a pressure between 0.01 and 1000 bar, preferably at 0.1 to 100 bar.

The reaction in process stage c) is preferably effected over a reaction time of from $1*10^{-7}$ to 1000 h.

Preferably, the ethylenedialkylphosphinic salt (III) removed after process stage c) from the reaction mixture by filtration and/or centrifugation is dried.

Preferably, the product mixture obtained after process stage b) is reacted with the metal compounds without further purification.

Preferred solvents are the solvents mentioned in process step a).

The reaction in process stage b) and/or c) is preferably effected in the solvent system given by stage a).

The reaction in process stage c) is preferably in a modified given solvent system. Acidic components, solubilizers, foam inhibitors, etc are added for this purpose.

In a further embodiment of the process, the product mixture obtained after process stage a), b) and/or c) is worked up.

In a further embodiment of the process, the product mixture obtained after process stage b) is worked up and thereafter the ethylenedialkylphosphinic acids (III), and/or salts or esters thereof, obtained after process stage b) are reacted in process stage c) with the metal compounds.

Preferably, the product mixture after process stage b) is worked up by isolating the ethylenedialkylphosphinic acids (III), and/or salts or esters thereof, by removing the solvent system, for example by evaporative concentration.

Preferably, the ethylenedialkylphosphinic salt Ill of the metals Mg, Ca, Al, Zn, Ti, Sn, Zr, Ce or Fe selectively has a residual moisture content of 0.01% to 10% by weight, preferably of 0.1% to 1% by weight, an average particle size of 0.1 to 2000 µm, preferably of 10 to 500 µm, a bulk density of 80 to 800 g/l, preferably of 200 to 700 g/l, and a Pfrengle flowability of 0.5 to 10, preferably of 1 to 5.

The moldings, films, filaments and fibers more preferably contain from 5% to 30% by weight of the ethylenedialkylphosphinic acid/ester/salts produced in accordance with one or more of claims 1, 3, 7 and 8, from 5 to 80% by weight of polymer or mixtures thereof, from 5 to 40% by weight of additives and from 5 to 40% by weight of filler, where the sum of the components is always 100% by weight.

The additives preferably comprise antioxidants, antistats, blowing agents, further flame retardants, heat stabilizers, impact modifiers, processing aids, lubricants, light stabilizers, antidripping agents, compatibilizers, reinforcing agents, fillers, nucleus-forming agents, nucleating agents, additives for laser marking, hydrolysis stabilizers, chain extenders, color pigments, softeners, plasticizers and/or plasticizing agents.

Preference is given to a flame retardant containing 0.1 to 90% by weight of the ethylenedialkylphosphinic acid, esters and salts (III), and 0.1% to 50% by weight of further additives, more preferably diols.

Preferred additives are also aluminum trihydrate, antimony oxide, brominated aromatic or cycloaliphatic hydrocarbons, phenols, ethers, chloroparaffin, hexachlorocyclopentadiene adducts, red phosphorus, melamine derivatives, melamine cyanurates, ammonium polyphosphates and magnesium hydroxide. Preferred additives are also further flame retardants, more particularly salts of dialkylphosphinic acids.

More particularly, the present invention relates to the use of the inventive ethylenedialkylphosphinic acid, esters and salts (III) as flame retardants or as an intermediate in the manufacture of flame retardants for thermoplastic polymers such as polyesters, polystyrene or polyamide and for thermoset polymers such as unsaturated polyester resins, epoxy resins, polyurethanes or acrylates.

Suitable polyesters derive from dicarboxylic acids and their esters and diols and/or from hydroxycarboxylic acids or the corresponding lactones.

It is particularly preferable to use terephthalic acid and ethylene glycol, 1,3-propanediol and 1,3-butanediol.

Suitable polyesters include polyethylene terephthalate, polybutylene terephthalate (Celanex® 2500, Celanex® 2002, from Celanese; Ultradur®, from BASF), poly-1,4-dimethylolcyclohexane terephthalate, polyhydroxybenzoates, and also block polyether esters derived from polyethers having hydroxyl end groups; and also polyesters modified with polycarbonates or MBS.

Synthetic linear polyesters having permanent flame retardancy are composed of dicarboxylic acid components, diol components of the present invention ethylenedialkylphosphinic acids and esters, or of the ethylenedialkylphosphinic acids and esters produced by the process of the present invention as phosphorus-containing chain members. The phosphorus-containing chain members account for 2-20% by weight of the dicarboxylic acid component of the polyester. The resulting phosphorus content in the polyester is preferably 0.1-5% by weight, more preferably 0.5-3% by weight.

The following steps can be carried out with or by addition of the compounds produced in accordance with the present invention.

Preferably, the molding material is produced from the free dicarboxylic acid and diols by initially esterifying directly and then polycondensing.

When proceeding from dicarboxylic esters, more particularly dimethyl esters, it is preferable to first transesterify, and then to polycondense by using catalysts customary for this purpose.

Polyester production may preferably proceed by adding customary additives (crosslinking agents, matting agents and stabilizing agents, nucleating agents, dyes and fillers, etc.) in addition to the customary catalysts.

The esterification and/or transesterification involved in polyester production is preferably carried out at temperatures of 100-300° C., more preferably at 150-250° C.

The polycondensation in the polyester production preferably takes place at pressures between 0.1 to 1.5 mbar and temperatures of 150-450° C., more preferably at 200-300° C.

The flame-retardant polyester molding materials produced in accordance with the present invention are preferably used in polyester moldings.

Preferred polyester moldings are filaments, fibers, films and moldings containing mainly terephthalic acid as dicarboxylic acid component and mainly ethylene glycol as diol component.

The resulting phosphorus content in filaments and fibers produced from flame-retardant polyesters is preferably 0.1-18%, more preferably 0.5-15% by weight and in the case of films 0.2-15%, preferably 0.9-12% by weight.

Suitable polystyrenes are polystyrene, poly(p-methylstyrene) and/or poly(alpha-methylstyrene).

Suitable polystyrenes preferably comprise copolymers of styrene or alpha-methylstyrene with dienes or acrylic derivatives, for example styrene-butadiene, styrene-acrylonitrile, styrene-alkyl methacrylate, styrene-butadiene-alkyl acrylate and styrene-butadiene-alkyl methacrylate, styrene-maleic anhydride, styrene-acrylonitrile-methyl acrylate; mixtures of high impact strength from styrene copolymers and another polymer, for example a polyacrylate, a diene polymer or an ethylene-propylene-diene terpolymer; also block copolymers of styrene, for example styrene-butadiene-styrene, styrene-isoprene-styrene, styrene-ethylene/butylene-styrene or styrene-ethylene/propylene-styrene.

Suitable polystyrenes preferably also comprise graft copolymers of styrene or alpha-methylstyrene, for example styrene on polybutadiene, styrene on polybutadiene-styrene or polybutadiene-acrylonitrile copolymers, styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene, styrene and alkyl acrylates or alkyl methacrylates on polybutadiene, styrene and acrylonitrile on ethylene-propylene-diene terpolymers, styrene and acrylonitrile on poly(alkyl acrylate)s or poly(alkyl methacrylate)s, styrene and acrylonitrile on acrylate-butadiene copolymers, and also their mixtures, as are also known for example as ABS, MBS, ASA or AES polymers.

The polymers preferably comprise polyamides and copolyamides derived from diamines and dicarboxylic acids and/or from aminocarboxylic acids or the corresponding lactams, such as nylon-2,12, nylon-4, nylon-4,6, nylon-6, nylon-6,6, nylon-6,9, nylon-6,10, nylon-6,12, nylon-6,66, nylon-7,7, nylon-8,8, nylon-9,9, nylon-10,9, nylon-10,10, nylon-11, nylon-12, and so on. Such polyamides are known for example under the trade names Nylon®, from DuPont, Ultramid®, from BASF, Akulon® K122, from DSM, Zytel® 7301, from DuPont; Durethan® B 29, from Bayer and Grillamid®, from Ems Chemie.

Also suitable are aromatic polyamides proceeding from m-xylene, diamine and adipic acid; polyamides produced from hexamethylenediamine and iso- and/or terephthalic acid and optionally an elastomer as modifier, for example poly-2,4,4-trimethylhexamethyleneterephthalamide or poly-m-phenyleneisophthalamide, block copolymers of the aforementioned polyamides with polyolefins, olefin copolymers, ionomers or chemically bonded or grafted elastomers or with polyethers, for example with polyethylene glycol, polypropylene glycol or polytetramethylene glycol. Also EPDM- or ABS-modified polyamides or copolyamides; and also polyamides condensed during processing ("RIM polyamide systems").

The ethylenedialkylphosphinic acid/ester/salts produced in accordance with one or more of claims 1, 3, 7 and 8 are preferably used in molding materials further used for producing polymeric moldings.

It is particularly preferable for the flame-retardant molding material to contain from 5 to 30% by weight of ethylenedialkylphosphinic acids, salts or esters produced in accordance with one or more of claims 1, 3, 7 and 8, from 5 to 80% by weight of polymer or mixtures thereof, from 5 to 40% by weight of additives and 5 to 40% by weight of filler, where the sum of the components is always 100% by weight.

The present invention also relates to flame retardants containing ethylene-dialkylphosphinic acids, salts or esters produced in accordance with one or more of claims 1, 3, 7 and 8.

The present invention additionally relates to polymer molding materials and also polymer moldings, films, filaments and fibers containing the ethylene-dialkylphosphinic salts (III) of the metals Mg, Ca, Al, Zn, Ti, Sn, Zr, Ce or Fe produced in accordance with the present invention.

The examples which follow illustrate the invention.

Production, processing and testing of flame-retardant polymer molding materials and flame-retardant polymer moldings.

The flame-retardant components are mixed with the polymer pellets and any additives and incorporated on a twin-screw extruder (Leistritz LSM® 30/34) at temperatures of 230 to 260° C. (glassfiber-reinforced PBT) or of 260 to 280° C. (glassfiber-reinforced PA 66). The homogenized polymeric strand was drawn off, cooled in a water bath and then pelletized.

After sufficient drying, the molding materials were processed on an injection molding machine (Aarburg Allrounder) at melt temperatures of 240 to 270° C. (glassfiber-reinforced PBT) or of 260 to 290° C. (glassfiber-reinforced PA 66) to give test specimens. The test specimens are subsequently flammability tested and classified using the UL 94 (Underwriter Laboratories) test.

UL 94 (Underwriter Laboratories) fire classification was determined on test specimens from each mixture, using test specimens of thickness 1.5 mm.

The efficacy of the ethylenediethylphosphinic acid (of the formula (III)) was examined by developing formulations with which it was possible to produce polymer moldings. Essentially, these formulations comprise phosphorus-modified epoxy resins based on ethylenedialkylphosphinic acids, hardener, imidazole as a catalyst and optionally fillers or other ingredients.

Epoxy resins used with preference for the formulations are bisglycidyl ethers based on bisphenol A, bisphenol F and bisphenol S (reaction products of these bisphenols and epichlorohydrin) or oligomers thereof, polyglycidyl ethers of phenol/formaldehyde and/or cresol/formaldehyde novolacs, which have been rendered flame-retardant by reaction with ethylenedialkylphosphinic acids of the formula (III).

The hardeners used for the epoxy resins may, for example, be aliphatic, cycloaliphatic, aromatic and heterocyclic amines or polyamines, such as diaminodiphenylmethane derivatives, diaminodiphenyl ethers and diaminodiphenyl sulfones, such as bis(4-aminophenyl)methane, aniline-formaldehyde resins, bis(4-aminophenyl)sulfone, ethylenediamine, propane-1,3-diamine, hexamethylenediamine, diethylenetriamine, triethylenetetramine, aminoethylpiperazine, 2,2,4-trimethylhexane-1,6-diamine, m-xylylenediamine, bis(4-aminocyclohexyl)methane, 2,2-bis(4-aminocyclohexyl)propane, 3-aminomethyl-3,5,5-trimethylcyclohexylamine (isophoronediamine), polyamidoamines, cyanoguanidines such as dicyandiamide, polyphenols such as 2,2-bis(4-hydroxyphenyl)propane (bisphenol A), cresol novolacs, phenol novolacs and bisphenol A novolacs, polycarboxylic acids and anhydrides thereof, for example phthalic anhydride, maleic anhydride, tetrahydrophthalic anhydride. In the examples which follow, preferably bisphenol A novolacs, phenol novolacs were used as hardeners for the phosphorus-modified epoxy resin.

Preferred catalysts or accelerators for production of the polymer moldings are imidazoles such as 1-methylimidazole, 2-methylimidazole, 2-ethyl-4-methyl-imidazole, 2-phenylimidazole, 2-heptadecylimidazole, and amines such as benzyldimethylamine or n-alkylpyridines. In the examples which follow, preferably 2-phenylimidazole was used as an accelerator.

A preferred ethylenedialkylphosphinic acid of the formula (III) is ethylene-diethylphosphinic acid.

The flame-retardant epoxy resin formulations examined in the invention preferably contain 0.1 to 25 parts by mass of ethylenediethylphosphinic acid of the formula (III) per 100 parts by mass of epoxy resin.

The formulation may additionally further comprise at least one filler. The filler may be inorganic, such as kaolin, talc, quartz flour, silicon dioxide, cristobalite, chalk, sheet silicates, for example bentonites or montmorillonites, mica powder, glass powder, glass beads, pulverized glass beads, aluminum oxide, wollastonite and magnesium hydroxide, or organic, such as polyamides, polyethylene, polyester or hardened epoxy resins. Other flame retardants such as aluminum trihydroxide, melamine, melamine derivatives of cyanuric acid, melamine derivatives of isocyanuric acid, melamine salts such as melamine phosphate, melamine polyphosphate or melamine diphosphate or ammonium polyphosphate, may likewise be used.

The inventive formulation may also comprise other additives which are used conventionally in epoxy resin formulations, such as pigments, dyes and stabilizers.

The UL 94 fire classifications are as follows:
V-0: Afterflame time never longer than 10 sec, total of afterflame times for 10 flame applications not more than 50 sec, no flaming drops, no complete consumption of the specimen, afterglow time for specimens never longer than 30 sec after end of flame application
V-1: Afterflame time never longer than 30 sec after end of flame application, total of afterflame times for 10 flame applications not more than 250 sec, afterglow time for specimens never longer than 60 sec after end of flame application, other criteria as for V-0
V-2: Cotton indicator ignited by flaming drops, other criteria as for V-1
Not classifiable (ncl): does not comply with fire classification V-2.

Some specimens examined were also tested for their LOI value. The LOI (Limiting Oxygen Index) value is determined to ISO 4589. According to ISO 4589, the LOI is the lowest oxygen concentration in volume percent which in a mixture of oxygen and nitrogen will support combustion of the plastic. The higher the LOI value, the greater the flammability resistance of the material tested.

| LOI | 23 | flammable |
| --- | --- | --- |
| LOI | 24-28 | potentially flammable |
| LOI | 29-35 | flame resistant |
| LOI | >36 | particularly flame-resistant |

Chemicals and Abbreviations Used
AIBN azobis(isobutyronitrile), (from WAKO Chemicals GmbH)
WakoV65 2,2'-azobis(2,4-dimethylvaleronitrile), (from WAKO Chemicals GmbH)
Deloxan® THP II metal scavenger (from Evonik Industries AG)

EXAMPLE 1

At room temperature, a three-neck flask equipped with stirrer and jacketed coil condenser is initially charged with 188 g of water, which is devolatilized by stirring and passing nitrogen through it. Then, under nitrogen, 0.2 mg of palladium(II) sulfate and 2.3 mg of tris(3-sulfophenyl)phosphine trisodium salt are added, the mixture is stirred, and then 66 g of phosphinic acid in 66 g of water are added. The reaction solution is transferred to a 2 l Büchi reactor and contacted with ethylene under superatmospheric pressure while stirring, and the reaction mixture is heated to 80° C. After 28 g of ethylene have been taken up, the system is cooled down and free ethylene is discharged. The reaction mixture is freed of solvent on a rotary evaporator. The residue is admixed with 100 g of demineralized water and stirred under a nitrogen atmosphere at room temperature, then filtered, and the filtrate is extracted with toluene, thereafter freed of solvent on a rotary evaporator and the ethylphosphonous acid obtained is collected. Yield: 92 g (98% of theory).

EXAMPLE 2

As in example 1, 99 g of phosphinic acid, 396 g of butanol, 42 g of ethylene, 6.9 mg of tris(dibenzylideneacetone)dipalladium and 9.5 mg of 4,5-bis(diphenylphosphino)-9,9-dimethylxanthene are reacted, then the product is purified by passing it through a column charged with Deloxan® THP II, and then n-butanol is added once again. At a reaction temperature of 80-110° C., the water formed is removed by azeotropic distillation. The product (butyl ethylphosphonite) is purified by distillation under reduced pressure. Yield: 189 g (84% of theory).

EXAMPLE 3

As in example 1, 198 g of phosphinic acid, 198 g of water, 84 g of ethylene, 6.1 mg of palladium(II) sulfate and 25.8 mg of 9,9-dimethyl-4,5-bis(diphenylphosphino)-2,7-sulfonatoxanthene disodium salt are reacted, then the product is purified by passing it through a column charged with Deloxan® THP II, and then n-butanol is added. At a reaction temperature of 80-110° C., the water formed is removed by azeotropic distillation. The product (butyl ethylphosphonite) is purified by distillation under reduced pressure. Yield: 374 g (83% of theory).

EXAMPLE 4

A 500 ml five-neck flask with gas inlet tube, thermometer, jacketed coil condenser and reflux condenser with gas incineration is initially charged with 94 g (1 mol) of ethylphosphonous acid (prepared as in example 1). Ethylene oxide is introduced at room temperature, a reaction temperature of 70° C. is established and the reaction is allowed to continue at 80° C. for another hour. The amount of ethylene oxide taken up is 65.7 g. The acid number of the product is less than 1 mg KOH/g. 129 g (94% of theory) of 2-hydroxyethyl ethylphosphonite is obtained as a clear colorless product.

EXAMPLE 5

In a 1 l 5-neck flask equipped with gas inlet frit, thermometer, stirrer, reflux condenser and initiator metering system, a solution of 94.0 g of ethylphosphonous acid (prepared as in example 1) is dissolved in 200 g of glacial acetic acid and heated to approx. 90° C. While stirring, a solution of 11.4 g of ammonium peroxodisulfate in 30 g of water is metered in over a period of 5 h. At the same time, approx. 10 l/h of acetylene are passed through the solution via the gas inlet frit. In the course of this, the reaction temperature is kept at approx. 100° C. After removal of the acetylene by means of passage of nitrogen, the mixture is allowed to cool, in the course of which ethylenebis(ethylphosphinic acid) precipitates out in the form of colorless crystals. These are filtered off and washed with acetic acid. Yield: 86.7 g (81% of theory).

EXAMPLE 6

In a 1 l 5-neck flask equipped with gas inlet frit, thermometer, stirrer, reflux condenser and initiator metering system, a solution of 188.0 g of ethylphosphonous acid (prepared as in example 1) is dissolved in 200 g of glacial acetic acid and heated to approx. 90° C. While stirring, a solution of 19 g of 2,2'-azobis(2-methylbutyronitrile) in 100 g of glacial acetic acid is metered in over a period of 6 h. At the same time, approx. 15 l/h of acetylene is passed through the solution via the gas inlet frit. In the course of this, the reaction temperature is kept at approx. 100° C. After removal of the acetylene by means of passage of nitrogen, the mixture is allowed to cool, in the course of which ethylenebis(ethylphosphinic acid) precipitates out. The latter is filtered off and washed with acetic acid. Yield: 177.6 g (83% of theory).

EXAMPLE 7

321 g (1.5 mol) of ethylenebis(ethylphosphinic acid) (prepared as in example 5) are dissolved at 85° C. in 400 ml of toluene, and 888 g (12 mol) of butanol are added. At a reaction temperature of approx. 100° C., the water formed is removed by azeotropic distillation. After purification by chromatography, 401 g (83% of theory) of ethylenebis(ethylphosphinic acid butyl ester) are obtained.

EXAMPLE 8

321 g (1.5 mol) of ethylenebis(ethylphosphinic acid) (prepared as in example 6) are dissolved at 85° C. in 400 ml of toluene, and 409 g (6.6 mol) of ethylene glycol are added, and esterification is effected in a distillation apparatus with a water separator at approx. 100° C. over the course of 4 h. After the esterification has ended, the toluene and excess ethylene glycol are removed under reduced pressure. 448 g (99% of theory) of ethylenebis(ethylphosphinic acid 2-hydroxy-ethyl ester) are obtained as a colorless oil.

EXAMPLE 9

155 g (2.5 mol) of ethylene glycol and 0.4 g of potassium titanyloxalate are added to 326 g (1 mol) of ethylenebis(ethylphosphinic acid butyl ester) (prepared according to example 7), and the mixture is stirred at 200° C. for 2 h. By gently evacuating, volatile components are distilled off. 296 g (98% of theory) of ethylenebis(ethylphosphinic acid 2-hydroxyethyl ester) are obtained.

EXAMPLE 10

A 500 ml five-neck flask with a gas inlet tube, thermometer, jacketed coil condenser and reflux condenser with gas incineration is initially charged with 214 g (1 mol) of ethylenebis (ethylphosphinic acid) (prepared as in example 6). At room temperature, ethylene oxide is introduced. Cooling is used to establish a reaction temperature of 70° C., and reaction is allowed to continue at 80° C. for another hour. The amount of ethylene oxide taken up is 64.8 g. The acid number of the product is less than 1 mg KOH/g. 257 g (95% of theory) of ethylenebis-(ethylphosphinic acid 2-hydroxyethyl ester) are obtained as a clear colorless liquid.

EXAMPLE 11

642 g (3 mol) of ethylenebis(ethylphosphinic acid) (prepared as in example 5) are dissolved in 860 g of water and initially charged in a 5 l five-neck flask with a thermometer, reflux condenser, jacketed coil condenser and dropping funnel, and neutralized with approx. 960 g (12 mol) of 50% sodium hydroxide solution. At 85° C., a mixture of 2583 g of a 46% aqueous solution of $Al_2(SO_4)_3 \cdot 14\ H_2O$ is added. Subsequently, the resulting solid is filtered off, washed with hot water and dried at 130° C. under reduced pressure. Yield: 642 g (93% of theory) of ethylenebis(ethylphosphinic acid) aluminum(III) salt as a colorless salt.

EXAMPLE 12

214 g (1 mol) of ethylenebis(ethylphosphinic acid (prepared as in example 6) and 170 g of titanium tetrabutoxide are heated in 500 ml of toluene under reflux for 40 hours. Butanol formed is distilled off from time to time with fractions of toluene. The solution formed is subsequently freed of the solvent. This gives 229 g of ethylenebis(ethylphosphinic acid) titanium salt.

EXAMPLE 13

290 g of terephthalic acid, 188 g of ethylene glycol and 0.34 g of zinc acetate are added to 39.1 g of ethylenebis (ethylphosphinic acid 2-hydroxyethyl ester) (prepared as in example 10), and the mixture is heated to 200° C. for 2 h. Then 0.29 g of trisodium phosphate anhydrate and 0.14 g of antimony(III) oxide are added, and the mixture is heated to 280° C. and then evacuated.

The resulting melt (363 g, phosphorus content: 2.2%) is used to injection-mold specimens of thickness 1.6 mm for the measurement of the oxygen index (LOI) to ISO 4589-2, and also for the UL 94 fire test (Underwriter Laboratories).

The specimens thus produced gave an LOI of 42 and fulfilled the V-0 fire class according to UL 94. Corresponding specimens not containing ethylenebis(ethylphosphinic acid 2-hydroxyethyl ester) gave an LOI of only 31 and fulfilled only the V-2 fire class according to UL 94. The polyester moldings comprising ethylenebis(ethylphosphinic acid 2-hydroxyethyl ester) thus exhibit marked flame-retardant properties.

EXAMPLE 14

12.9 g of 1,3-propylene glycol were added to 19.6 g of ethylenebis(ethylphosphinic acid) (prepared analogously to example 5), and the water formed in the esterification was removed at 160° C. Then 378 g of dimethyl terephthalate, 192 g of 1,3-propanediol, 0.22 g of tetrabutyl titanate and 0.05 g of lithium acetate were added, and the mixture was first heated to 130 to 180° C. while stirring for 2 h, then to 270° C. under reduced pressure. The polymer (418 g) contains 1.4% phosphorus; the LOI is 38.

EXAMPLE 15

367 g of dimethyl terephthalate, 238 g of 1,4-butanediol, 0.22 g of tetrabutyl titanate and 0.05 g of lithium acetate are added to 19.7 g of ethylenebis(ethylphosphinic acid) (prepared as in example 6), and the mixture is heated first to 130 to 180° C. while stirring for 2 h, then to 270° C. under reduced pressure. The polymer (432 g) contains 1.3% phosphorus; the LOI is 34, that of untreated polybutylene terephthalate being only 23.

EXAMPLE 16

In a 250 ml five-neck flask with reflux condenser, stirrer, thermometer and nitrogen inlet, 100 g of a bisphenol A bisglycidyl ether with an epoxy value of 0.55 mol/100 g (Beckopox EP 140, from Solutia) and 13.9 g (0.13 mol) of ethylenebis(ethylphosphinic acid) (prepared analogously to example 5) are heated to a maximum of 150° C. while stirring. After 30 min, this gives a clear melt. After a further hour of stirring at 150° C., the melt is cooled and crushed with a mortar. This gives 117.7 g of a white powder with a phosphorus content of 3.5% by weight.

EXAMPLE 17

In a 2 l flask with stirrer, water separator, thermometer, reflux condenser and nitrogen inlet, 29.4 g of phthalic anhydride, 19.6 g of maleic anhydride, 24.8 g of propylene glycol, 20.4 g of ethylenebis(ethylphosphinic acid 2-hydroxyethyl ester) (prepared as in example 10), 20 g of xylene and 50 mg of hydroquinone are heated to 100° C. while stirring and passing nitrogen through. When the exothermic reaction sets in, the heating is removed. After the reaction has abated, the mixture continues to be stirred at approx. 190° C. After 14 g of water have separated out, the xylene is distilled off and the polymer melt is cooled. This gives 86.2 g of a white powder having a phosphorus content of 4.8% by weight.

EXAMPLE 18

A mixture of 50% by weight of polybutylene terephthalate, 20% by weight of 3-ethylenebis(ethylphosphinic acid) aluminum(III) salt (prepared as in example 11) and 30% by weight of glass fibers compounded on a twin-screw extruder (Leistritz LSM 30/34) at temperatures of 230 to 260° C. to give a polymer molding material. The homogenized polymer strand is drawn off, cooled in a water bath and then pelletized. After drying, the molding materials are processed on an injection molding machine (Aarburg Allrounder) at 240 to 270° C. to give polymer moldings, and a UL-94 classification of V-0 is determined.

EXAMPLE 19

A mixture of 53% by weight of nylon-6,6, 30% by weight of glass fibers and 17% by weight of 3-ethylenebis(ethylphosphinic acid) titanium salt (prepared as in example 12) is compounded on a twin-screw extruder (Leistritz LSM 30/34) to give polymer molding materials. The homogenized polymer strand is drawn off, cooled in a water bath and then pelletized. After drying, the molding materials are processed on an injection molding machine (Aarburg Allrounder) at 260 to 290° C. to give polymer moldings, and a UL-94 classification of V-0 is obtained.

The epoxy resin formulations described further up were used to produce polymer moldings. For this purpose, the individual components are weighed out and mixed with one another in a suitable vessel at high stirrer speed. Room temperature solid resins are melted beforehand. After mixing, the resin mixture is devolatilized by applying reduced pressure.

The finished resin mixture is introduced into a suitable casting mold and hardened at room temperature or in a drying cabinet. The thickness of the polymer moldings produced was 3 mm or 1.6 mm.

In addition to the flammability class according to UL 94, the Charpy impact resistance and the hydrolysis stability were preferably tested on the polymer moldings produced.

To determine the hydrolysis stability, polymer moldings were stored in each case at 100° C. in 80 ml of water for 24 h. After storage, the phosphorus content of the water was determined.

In the studies conducted, it was found that ethylenediethylphosphinic acid, in addition to very good flame-retardant action, also reduces the brittleness of the hardened epoxy resin matrix, and is not hydrolyzed in the course of water storage.

The result is explained hereinafter by additional examples:
To produce the flame-retardant epoxy resin formulations, the following compounds were used:
Beckopox® EP 140 (BPA-EP resin, Solutia, United States)
PF® 0790 K04 (phenol novolac, Hexion Chemical, United States)
2-Phenylimidazole (Degussa/Trostberg, Germany)
TS-601 (aluminum trihydroxide, Martinswerk, Germany)
DOPO®-HQ (10-(2,5-dihydroxyphenyl)-10H-9-oxa-10-phospha-phenanthrene 10-oxide,Sanko Co., Ltd., Japan)

EXAMPLE 20 a) Preparation of a Phosphorus-modified Epoxy Resin Based on Ethylenediethylphosphinic Acid A four-neck flask equipped with reflux condenser, thermocouple, nitrogen inlet and stirrer is initially charged with 100 g of Beckopox® EP 140, EP value 180 g/mol. While stirring, the mixture is heated to 110° C. and residual water is removed under reduced pressure, followed by ventilation with dry nitrogen. Thereafter, the temperature in the flask is increased to 130° C., and 11.7 g of ethanebisethylphosphinic acid are added while stirring with nitrogen flow. The temperature of the reaction mixture is increased to 160° C. and maintained for 1 h. The product is subsequently poured out while hot and cooled. This gave a phosphorus-modified epoxy resin with a phosphorus content of 3% and an epoxy equivalent of 267 g/mol.

The proportion of phosphorus in the epoxy resin was varied correspondingly by means of different amounts of ethanebisethylphosphinic acid in the synthesis (examples 20 a) 1-a) 4).

b) Preparation of a Phosphorus-modified Epoxy Resin Based on DOPO-HCA (Comparative Example, 20 b))

A four-neck flask equipped with reflux condenser, thermocouple, nitrogen inlet and stirrer is initially charged with 100 g of Beckopox® EP 140, EP value 180 g/mol. While stirring, the mixture is heated to 110° C. and residual water is removed under reduced pressure, followed by ventilation with dry nitrogen. Thereafter, the temperature in the flask is increased to 130° C., and 19 g of DOPO(HCA-HQ) are added while stirring with nitrogen flow. The temperature of the reaction mixture is increased to 160° C. and kept there for 2.5 h. The product is subsequently poured out while hot and cooled.

A phosphorus-modified epoxy resin with a phosphorus content of 1.5% and an epoxy equivalent of 286 g/mol was obtained.

Table 1 shows the combination of the ethanebisethylphosphinic acid with a bisphenol A novolac as a hardener and in an example with an additional flame retardant. The accelerator used was 2-phenylimidazole.

As can be inferred from table 1, at a concentration of in the P resin, a V-0 classification was attained both at thickness 3 mm and at 1.6 mm. The impact resistances of the polymer moldings produced with these formulations were always at a higher level compared to the reference example. In the water used for the hydrolysis, moreover, no phosphorus was found. Accordingly, the ethanebisethylphosphinic acid is not hydrolyzed and then washed out of the thermoset network in the course of water storage.

TABLE 1

| | | Example 20 | | | | |
|---|---|---|---|---|---|---|
| | | a) 1 | a) 2 | a) 3 | a) 4 | b) (V)* |
| Resin formulation | P-modified EP resin based on ethanebis(ethylphosphinic acid) | 100 | 100 | 100 | 100 | — |
| | P-modified EP resin based on DOPO-HQ | — | — | — | — | 100 |
| | Phenol novolac | 34 | 43 | 46 | 46 | 37 |
| | 2-Phenylimidazole | 0.03 | 0.03 | 0.03 | 0.03 | 0.03 |
| | Aluminum trihydroxide (TS601) | — | — | — | 25 | — |
| Properties of the polymer molding | P content in the test specimen [%] | 2.6 | 1.8 | 1.3 | 1.3 | 1.1 |
| | Charpy impact resistance [kJ/cm²] | 50 | 44 | 35 | 30 | 26 |
| | P content in water after storage at 100° C. [ppm] | <1 | <1 | <1 | <1 | <1 |
| | UL94 | V-0 | V-0 | V-1 | V-0 | V-0 |

*(V) = Comparative example

The invention claimed is:

1. A process for preparing ethylenedialkylphosphinic acids, or salts or esters thereof comprising the steps of a) reacting a phosphinic acid source (I)

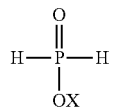

(I)

with olefins IV

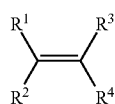

(IV)

in the presence of a catalyst A to give an alkylphosphonous acid (II), or salt or ester thereof,

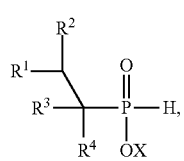

(II)

b) reacting the alkylphosphonous acid (II), or salt or ester thereof with at least one acetylenic compound (V)

(V)

in the presence of at least one catalyst B to give an ethylenedialkylphosphinic acid derivative (III)

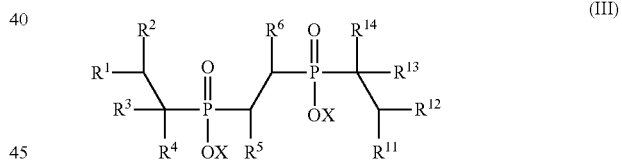

(III)

where $R^1$-$R^6$ are each H, $R^{11}$-$R^{14}$ are each H, X is H, Ca, Mg, Al, Zn, Ti, Mg, Ce, Fe, methyl, ethyl, n-propyl, isopropyl, n-butyl, isobutyl, tert-butyl, phenyl, 2-hydroxethyl, 2-hydroxypropyl, 3-hydroxypropyl, 4-hydroxybutyl, allyl, glycerol or a combination thereof and the catalyst A is a transition metal or a transition metal compound catalyst system comprising of a transition metal or a transition metal compound and at least one ligand, and the catalyst B is peroxide-forming compound, peroxo compound, azo compound or a combination thereof selected from the group consisting of hydrogen peroxide, sodium peroxide, lithium peroxide, potassium persulfate, sodium persulfate, ammonium persulfate, sodium peroxodisulfate, potassium peroxoborate, peracetic acid, benzoyl peroxide, di-t-butyl peroxide, peroxodisulfuric acid, azodiisobutyronitrile, 2,2'-azobis(2-amidinopropane) dihydrochloride, 2,2'-azobis(N,N'-dimethyleneisobutyramidine) dihydrochloride and a combination thereof.

2. The process as claimed in claim 1, wherein the ethylenedialkylphosphinic acid (III), or salt or ester thereof, obtained after step b) is reacted, in a step c), with a metal compound, a protonated nitrogen base or a combination thereof, wherein the metal compound is Mg, Ca, Al, Sb, Sn, Ge, Ti, Fe, Zr, Ce, Bi, Sr, Mn, Li, Na or K to yield ethylenedialkylphosphinic acid salts (III) of the metal compound, of the nitrogen base or a combination thereof.

3. The process as claimed in claim 1, wherein the alkylphosphonous acid (II), salt or ester thereof, obtained after step a), the ethylenedialkylphosphinic acid (III), or salt or ester thereof, obtained after step b), or a combination thereof is esterified with an alkylene oxide or a branched, staturated or unsaturated, monohydric or polyhydric alcohol having a carbon chain length of $C_1$-$C_{18}$ or a combination thereof, and the resulting alkylphosphonous ester (II) or ethylenedialkylphosphinic ester (III) formed is subjected to the further reaction step b).

4. The process as claimed in claim 1, wherein the transition metal or the metal in the transition metal compound is selected from the seventh or eighth transition groups.

5. The process as claimed in claim 1, wherein the transition metal or the metal in the transition metal compounds is rhodium, nickel, palladium, platinum, ruthenium or a combination thereof.

* * * * *